(12) United States Patent
Martakos et al.

(10) Patent No.: US 6,774,155 B2
(45) Date of Patent: Aug. 10, 2004

(54) METHOD FOR TREATING POLYMER MATERIALS AND PRODUCTS PRODUCED THEREFROM

(75) Inventors: Paul Martakos, Pelham, NH (US); Thomas M. Swanick, Milford, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 169 days.

(21) Appl. No.: 10/196,692

(22) Filed: Jul. 16, 2002

(65) Prior Publication Data

US 2003/0149126 A1 Aug. 7, 2003

Related U.S. Application Data

(62) Division of application No. 09/400,813, filed on Sep. 22, 1999, now Pat. No. 6,573,311.

(51) Int. Cl.[7] .................................................. C08F 2/48
(52) U.S. Cl. .................... 522/157; 522/150; 522/155; 522/156; 522/161; 264/446; 264/464; 264/469; 264/423; 623/11.11; 623/18.11; 623/20.11; 623/22.11; 623/66.11; 424/422; 424/423
(58) Field of Search ........................... 522/157, 150, 522/155, 156, 161; 264/446, 464, 469, 423; 623/11.11, 18.11, 20.11, 22.11, 66.11; 424/422, 423

(56) References Cited

U.S. PATENT DOCUMENTS

| | | | |
|---|---|---|---|
| 3,878,164 A | 4/1975 | Lott | 260/42.27 |
| 4,718,907 A | 1/1988 | Karwoski | 623/12 |
| 4,973,609 A | 11/1990 | Browne | 521/81 |
| 5,066,565 A | 11/1991 | Martinez et al. | 430/296 |
| 5,389,195 A | 2/1995 | Ouderkirk et al. | 156/643 |
| 5,403,453 A | 4/1995 | Roth et al. | 204/164 |
| 5,403,524 A | 4/1995 | Bürger et al. | 264/22 |
| 5,426,128 A | 6/1995 | Bürger et al. | 521/134 |
| 5,433,909 A | 7/1995 | Martakos et al. | 264/209.1 |
| 5,437,900 A | 8/1995 | Kuzowski | 428/36.1 |
| 5,462,781 A | 10/1995 | Zukowski | 428/36.1 |
| 5,474,824 A | 12/1995 | Martakos et al. | 428/36.9 |
| 5,501,827 A | 3/1996 | Deeney et al. | 264/460 |

FOREIGN PATENT DOCUMENTS

| | | |
|---|---|---|
| DE | 4141805 | 6/1993 |
| EP | 616004 | 9/1994 |

OTHER PUBLICATIONS

Dillingham, G. and Winter, G. "Plasma Processing" PC pp. 10–14 (Dec. 1998).

Primary Examiner—James J. Seidleck
Assistant Examiner—Sanza L. McClendon
(74) Attorney, Agent, or Firm—Lahive & Cockfield, LLP

(57) ABSTRACT

The invention is directed to methods for fabricating devices from polymer precursors, along with devices so fabricated. The methods of the invention include the steps of plasma treating a polymer based resin, paste, preform billet, or extrudate, and employing the treated polymer in the fabricated device. According to one embodiment, the fabricated device can include implantable prosthetics such as heart valves, sutures, vascular access devices, vascular grafts, shunts, catheters, single layered membranes, double layered membranes, and the like. Devices fabricated according to one embodiment of the invention include regions having selected porosity, permeability and/or chemistry characteristics.

58 Claims, 14 Drawing Sheets

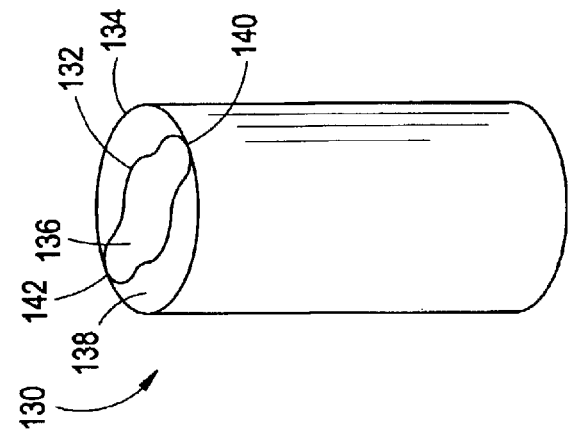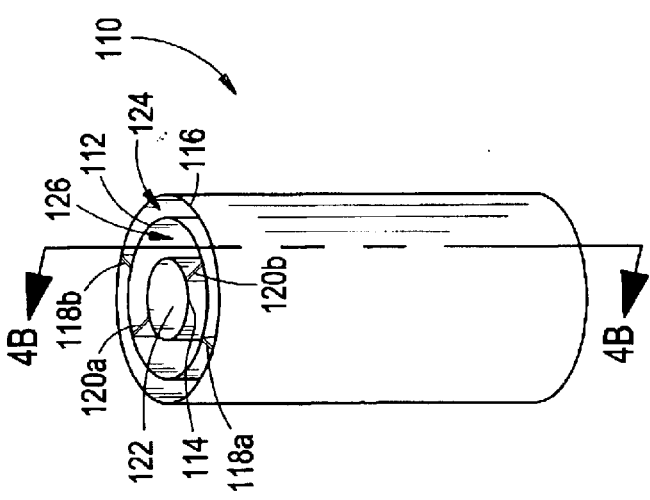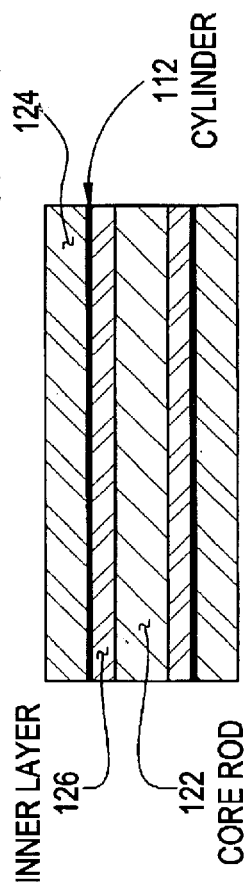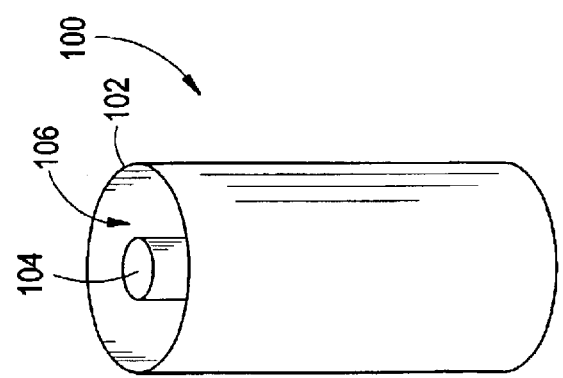

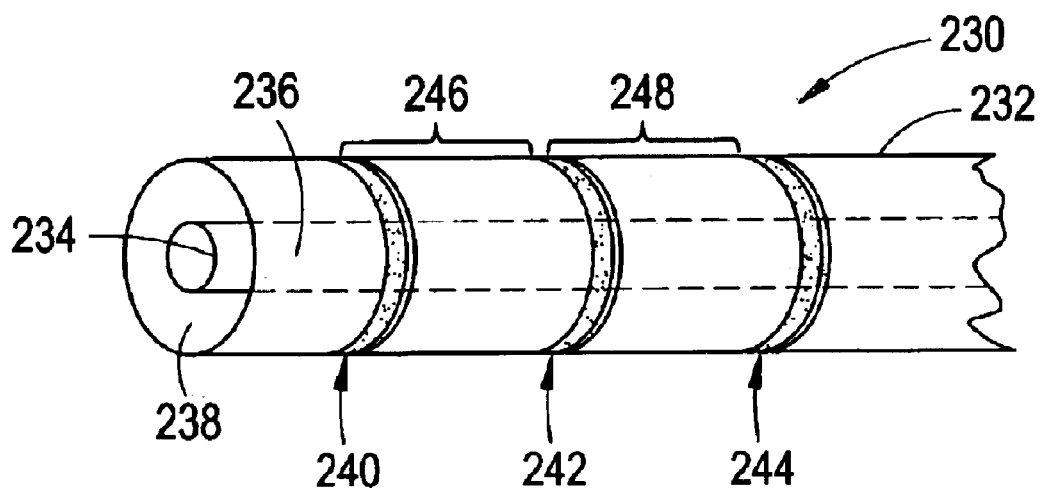
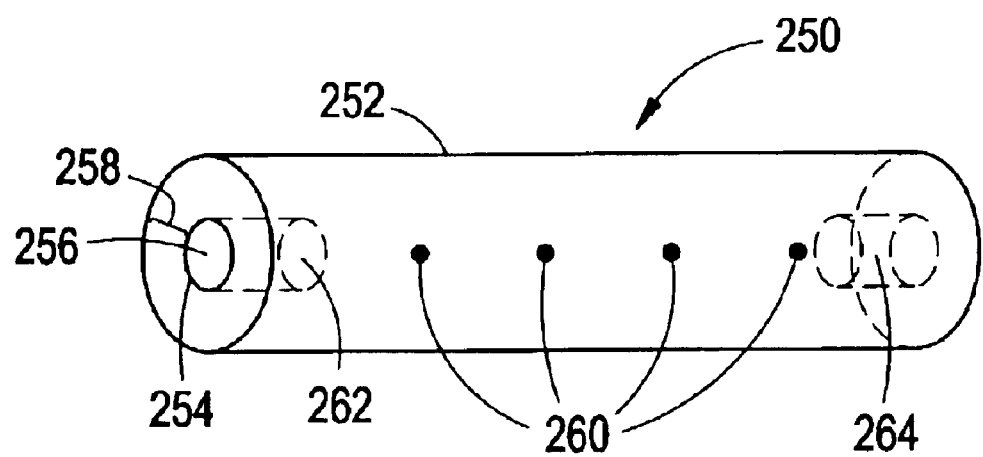

METHOD FOR TREATING POLYMER MATERIALS AND PRODUCTS PRODUCED THEREFROM

This application is a divisional application of U.S. application Ser. No. 09/400,813, filed on Sep. 22, 1999, now U.S. Pat. No. 6,573,311. The contents of the aforementioned application are hereby incorporated by reference. The present invention relates generally to methods for treating polymer and to products produced therefrom. More particularly, the invention relates to methods for treating polymer resins prior to final processing of those materials, and for fabricating articles from polymer materials so treated.

TECHNICAL FIELD

BACKGROUND OF THE INVENTION

Polymers are materials having long chemical chains composed of many repeat units. Polymers are prepared using monomer units which undergo a chemical reaction resulting in formation of repeat chemical bonds arranged into long chain structures having relatively high molecular weights. These polymers can exist in a solid or liquid state and are typically called resins. Resins are then processed using techniques such as extrusion, molding, forming, and casting, to fabricate products with desired properties for various applications.

There are various types of polymer resins, often classified according to their polymerization chemistry and fabrication processes. Classifications include: thermoplastics which soften and flow when heated during processing, thermosets which undergo a chemical change during processing, and engineering resins that are processed in a nonconventional manner. Fabrication methods pertinent to polymer resins include: molding processes in which finely divided plastic is forced by the application of heat and pressure to flow into, fill, and conform to the shape of a cavity (mold); calendering process used for the manufacture of sheet or film, whereby granular resin is passed between pairs of highly polished heated rolls under high pressure; casting processes, in which fine particles of resin are suspended in a liquid medium that are then allowed to flow onto a support substrate or large polished wheel; extrusion processes, in which the polymer resin is propelled continuously along a cylindrical barrel under controlled shear conditions, for example with the aid of a screw motion through regions of high temperature and pressure or with the aid of a ram piston, through a preshaped die. A wide variety of shapes can be made by extrusion, including rods, sheets, channels, and tubes.

Some polymers are also suitable for post processing after fabrication. One example of a post fabrication process is expansion after extrusion, which results in porous, flexible articles. Polymers suitable for expansion (such as polytetrafluoroethylene (PTFE), ultra high molecular weight polyethylene (UHMWPE), and polyethyleneterephthalate (PET) ) are composed of long polymer chains. Chain length determines molecular weight, and chain orientation dictates crystallinity.

UHMWPE polymer resin is processed in a manner similar to PTFE, using preformed billets and ram extrusion, although it is not necessary to add an extrusion aid because the material is less shear sensitive, followed by expansion and sintering under applied heat and force.

PET polymer resin is a long chain, highly crystalline polymer, that is extruded using conventional extrusion techniques to form an extruded article. The extruded article may then be expanded and/or stretched at elevated temperatures.

A known method of forming an article made of PTFE is to blend a powdered resin with a lubricant or extrusion aid and compress the combination under relatively low pressure into a preformed billet. Using a ram-type extruder, the billet is then extruded through a die having a desired cross-section. Next, the lubricant is removed from the extruded billet by drying or by another extraction method. The dried extruded material (hereinafter "extrudate"), is then stretched and/or expanded at elevated temperatures below the crystalline melting point of the resin. In the case of PTFE, this results in the material taking on a microstructure characterized by elongated nodes interconnected by fibrils. Typically, the nodes are oriented with their elongated axis perpendicular to the direction of stretching.

After stretching, the extrudate is sintered by heating it to a temperature above its crystalline melting point while being maintained in a stretched condition. This can be considered an amorphous locking process for permanently "locking-in" the microstructure in the expanded or stretched configuration.

Sometimes it may be desirable to modify the surface characteristics of articles made of PTFE. Conventional surface treatment approaches have been developed for modifying the surface characteristics of PTFE extruded substrates. According to one method, glow discharge plasma techniques, such as Radio Glow Discharge (RGD), are used to perform the surface modifications. Those surface modifications include plasma polymerization, plasma activation and plasma etching. Plasma polymerization entails using radio frequency gas plasma and polymerizing gases to polymerize a material onto a substrate surface. Plasma activation entails using a non-polymer forming gas, such as oxygen or a saturated fluorocarbon, to chemically modify a substrate surface. Plasma etching techniques employ reactive gas plasma to etch or roughen a surface by removing quantities of the substrate surface material. Etching can also be accomplished with other energy sources such as ion beams. Additionally, conventional masking techniques can be used in combination with etching to produce a desired textured pattern.

Prior publications directed toward surface treatments disclose a variety of motivations for performing surface modifications. By way of example, some prior approaches are directed to enhancing biocompatability, non-thrombogenic properties, wettability, adhesiveness, hydrophobicity, cleanliness and/or bacteriacidal properties of the polymeric substrate surface. Surface treatments are also employed to alter the porosity, permeability, or chemistry of a substrate surface region.

A drawback of conventional surface treatment approaches is that they operate on finished, fabricated and/or finally processed materials, thus rendering such approaches ineffective with regard to modifying bulk substrate properties, such as porosity and permeability. Additionally, chemistry modifications are limited to surface effects, as well as being limited to treating an entire article. As used herein, the term "chemistry" refers to the atomic elements that comprise particular materials, along with the concentration of each element included in the particular material.

A typical application for substrates having regions of selective porosity and chemistry characteristics the fabrication of vascular grafts. By way of example, it is sometimes desirable to fabricate grafts that are relatively porous on an outer surface to encourage tissue ingrowth and anchoring, but relatively nonporous on an inner surface so as not to promote thrombosis or leakage.

One conventional technique for tailoring porosity involves employing non-uniform lubrication levels in a preform. Other conventional approaches involve stacking preforms of different PTFE materials, PTFE and a dissimilar material, or preforms fabricated with different lubrication levels together and extruding a structure. Another prior approach is directed to surrounding an inner extruded PTFE tube with one or more additional concentric layers of tubing having selected porosities. Other conventional methods for varying substrate porosity attempt to modify the characteristics of polymeric resins. One such prior art method, irradiates a polymer powder resin with ionizing radiation, prior to compressing the resin into a billet. According to that method, polymeric powder resin is exposed to ionizing radiation in the range of 0.01–2 Mrad. As a result, the polymeric powder exhibits improved powder flow properties, and when combined with lubricants requires lower pressure to extrude the resultant paste then does paste formed with untreated resin. This method also discloses combining the treated powder with untreated resin and/or silica to achieve a variety of extrusion pressures and flow properties.

Another conventional approach for varying substrate porosity irradiates PTFE scraps at an energy dose ranging from 10–1000 kGy, where a Gy is an SI unit and is equivalent to a joule/kg. The irradiation process degrades the PTFE to have a relatively low average molecular weight of less than $10^6$. The process also lowers the melting temperature and reduces the particle size of the PTFE resin to range from 0.1–100 micrometers. The radiation-degraded PTFE can be combined with untreated PTFE, having a relatively higher molecular weight in the range of $1\times10^6$ to $50\times10^6$.

A drawback of conventional pre-extrusion irradiation methods is that they degrade the PTFE by reducing the molecular weight and particle size. While these methods produce materials that can be mixed with untreated PTFE, they fail to produce stand alone materials capable of extrusion.

SUMMARY OF THE INVENTION

The present invention is directed generally to methods for treating polymer resins and products produced therefrom. More particularly, the invention relates to methods for treating polymer resins prior to subsequent processing of hose resins, and to articles fabricated from polymer materials so treated. According to an illustrative process of the invention, a resin of an expandable polymer such as, polytetrafluoroethylene (PTFE), fluorinated ethylene propylene (FEP), perfluoroalkoxytetrafluoroethylene (PFA), ultra high mollecular weight polyethelene (UHMWPE) or polyetheleneterephthalate (PET)is provided. The resin is then treated with a plasma energy such as plasma glow discharge treatment, to a sufficient degree that the treatment effects a porosity, and/or a chemistry quality in articles fabricated from the treated resin. According to other embodiments, the plasma treatment effects other bulk properties of the resin, such as permeability, fibril density, and node size of articles fabricated from the treated resin.

According to one aspect of the invention, the plasma glow discharge treatment includes plasma polymerization onto the surface of a polymer resin. n an alternative embodiment, the plasma glow discharge treatment includes plasma activation of the resin. In a further embodiment of the invention, the plasma glow discharge treatment includes plasma etching of the resin. In one embodiment, the plasma glow discharge treatment includes a Radio Glow Discharge (RGD) treatment.

According to a further feature, a process of the invention employs the plasma energy treated resin in articles of manufacture. An illustrative process for incorporating the treated resin into an article of manufacture includes the steps of combining the treated resin with an extrusion aid to form a blended polymer paste, compressing the blended paste into a preformed billet, extruding the preformed billet into an extruded shape, and expanding and sintering the extruded article. According to a further feature, an illustrative process of the invention forms an implantable prosthesis from the sintered preformed billet. According to additional features, the implantable prosthesis may be, among other devices, vascular grafts, endovascular liners and grafts, prosthetic patches, vascular access devices, shunts, catheters, sutures or implantable tissue augmentation devices, such as those used in cosmetic surgery. According to yet a further feature, the articles of manufacture include single and multilayered membranes. Such membranes may be employed in clinical diagnostic test strips or in filtration devices.

According to one aspect of the invention, the polymer resin is subjected to the plasma discharge treatment. However, according to other embodiments, the blended paste formed from the polymer resin and the extrusion aid is subjected to the plasma discharge treatment. In alternative embodiments, preformed paste billets and unexpanded extrudates are subjected to the plasma treatment. As used herein, the term component refers to untreated polymer resins, pastes, preformed billets, and unexpanded extrudates formed from expandable polymers. According to other features of the invention, the blended treated pastes, preformed billets or unexpanded extrudates that are treated with plasma discharge are employed in fabricating articles, such as those mentioned above.

According to another aspect of the invention, polymer articles formed in accord with processes of the invention have regions of differing bulk characteristics, such as porosity, fibril density, node size (referred to collectively herein as porosity qualities), permeability, and chemistry. According to one embodiment, differently plasma discharge treated pastes, or pastes formed from differently treated resins are disposed in selected regions of a preform mold and compressed into a preformed billet. As a result, the subsequently extruded billet includes a plurality of regions having different bulk characteristics. In a related embodiment, differently treated pastes, or pastes formed from differently treated resins are disposed in preform molds having a plurality of chambers separated by discrete barriers. The chambers facilitate the formation of billets having configurable regions of selected bulk properties. According to a further feature of the invention, instead of being created by discrete barriers, the different regions having different bulk properties are merged through gradients, such as porosity gradients.

In an alternative embodiment, methods of the invention provide an improved polymer resin by introducing a polymer resin, such as PTFE, FEP, PFA, PET or UHMWPE resin, into a chamber and plasma glow discharge treating the resin. According to another embodiment, a method of the invention provides an improved blended paste by blending a resin of a polymer, such as PTFE, FEP, PFA, PET or UHMWPE, with an extrusion aid, such as ISOPAR-G or ISOPAR-H, available from Exxon Corporation, and plasma glow discharge treating the blended paste.

According to further aspects, the invention provides a variety of articles of manufacture, such as prosthetic devices and membranes, having selectable porosity and chemistry characteristics, and formed from polymer resins, pastes, preformed billets and unexpanded extrudates, each being treated with a plasma discharge.

BRIEF DESCRIPTION OF THE DRAWINGS

The subject matter regarded as the invention is particularly pointed out and distinctly claimed in the concluding portion of the specification. The invention, however, both as to organization and method of practice, together with further objects and advantages thereof, is best understood by reference to the following illustrative description taken in conjunction with the accompanying drawings in which like numerals refer to like elements.

FIG. 3 is a perspective view of a preform mold employed in an illustrative example of the invention;

FIG. 4A is a perspective view of an alternative preform mold employed in conjunction with an illustrative example of the invention;

FIG. 4B is a longitudinal cross-sectional view of the preform mold of FIG. 4A filled with treated and untreated PTFE paste;

FIG. 5 is a perspective view of another alternative preform mold employed in conjunction with an illustrative example of the invention;

FIG. 14 is a perspective view of a tubular billet formed in accord with an illustrative embodiment of the invention and having discrete axially extending bands, each band having a selective porosity and chemistry characteristic;

FIG. 15 is a perspective view of a preformed billet having an optional axial channel, formed in accord with an illustrative embodiment of the invention and having discrete regions of selective porosity and chemistry characteristics;

DESCRIPTION OF ILLUSTRATED EMBODIMENTS

As briefly described above, the present invention relates generally to methods for treating polymer resins and for fabricating articles using the treated materials. According to an illustrative embodiment, PTFE resin, paste or extrudate is exposed to a plasma energy treatment such as, a plasma glow discharge (PGD) treatment, and the treated material is employed in fabricating articles of manufacture. Although, the following illustrative embodiment is directed to PTFE and PGD treatment, skilled artisans will appreciate that the methods of the invention are equally applicable to other polymer resins such as, FEP, PFA, PET and UHMWPE; and other plasma energy treatments, such as, plasma etching and plasma activation.

An illustrative process of the invention alters the porosity characteristics of subsequently formed devices by treating substrate component materials, such as the resins, pastes, preformed billets and extrudates, prior to expansion and sintering. The illustrative methods according to the invention employ an RGD plasma activation treatment. However, other plasma radiation treatment methods, such as, plasma activation and plasma etching, are equally applicable. Unlike the prior art irradiation approaches, which degrade the component materials, such as the PTFE resins, the illustrative embodiments of the invention do not substantially alter the molecular weight or particle size of the fluoropolymer, and thus, do not mechanically degrade the component material.

As discussed in further detail below, substrates formed from component materials treated in accord with methods of the invention can have cross-sectional regions distinguished from other cross-sectional regions by different porosities. As such, the illustrative methods of the invention provide virtually unlimited possibilities for varying the porosity, permeability, and/or chemistry characteristics of polymeric substrates.

Additionally, the methods of the invention may be combined with prior methods, such as varying lubricant levels and irradiating fluoropolymer resins to realize new and unique porosity and/or chemistry characteristics.

Figure 1:
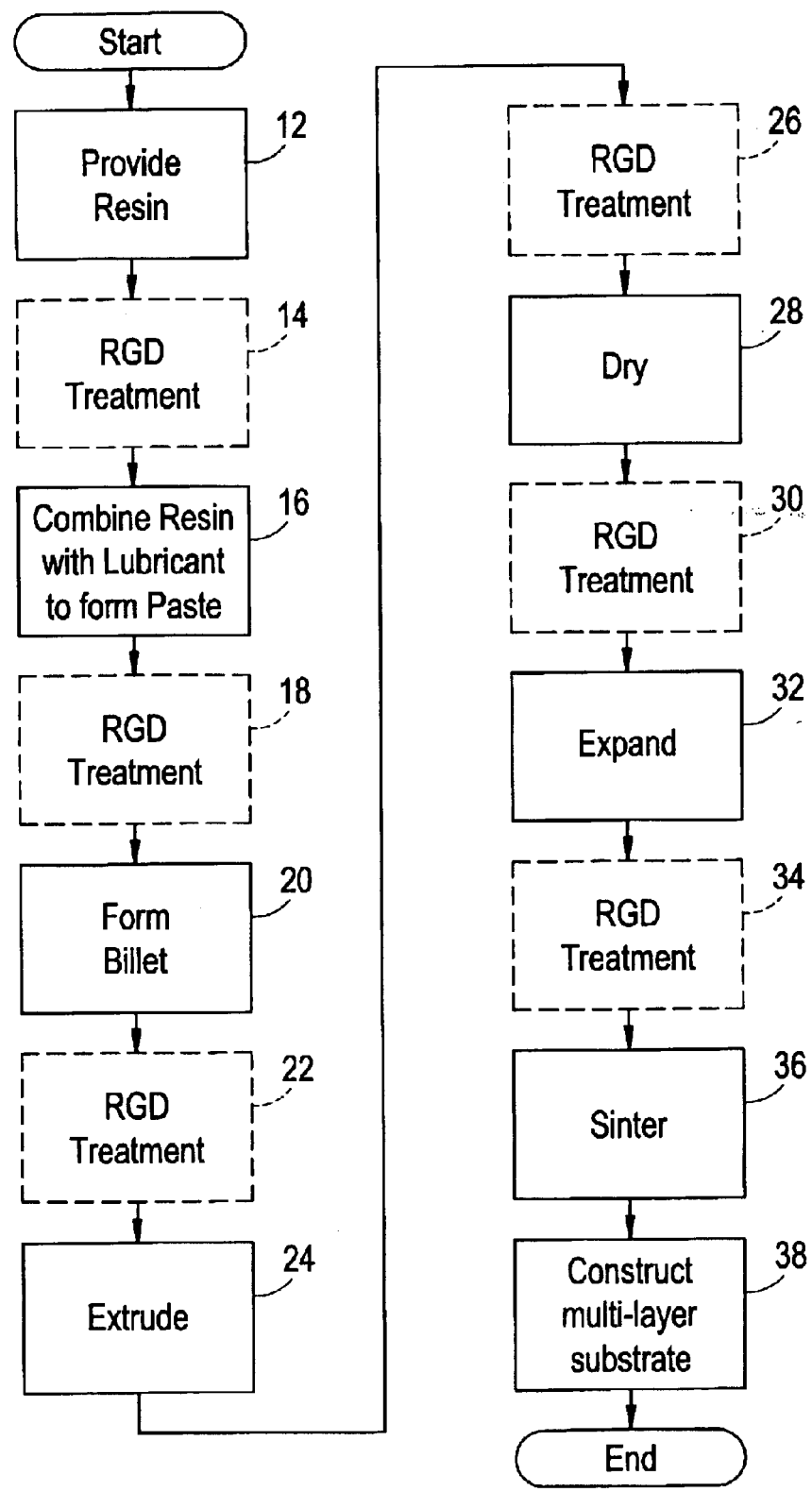
FIG. 1 is a flow chart illustrating steps performed by illustrative embodiments of the present invention.

FIG. 1 is a flow chart of a process for forming an article made of PTFE in accordance with the illustrative embodiment. Formation of an article begins with the provision of a PTFE resin (step 12). The resin is for example, Fluon CD-123, available from ICI Americas. The PTFE resin may then be subject to RGD treatment (step 14). As mentioned above, the RGD treatment may alter the permeability, porosity and/or chemistry characteristics of articles that have been fabricated with the resin. Step 14 is depicted in phantom form to note that it is optional. The RGD treatment may be performed at other stages of the formation of the article as will be described in more detail below.

The resin is combined with an extrusion aid or lubricant to form a blended resin paste (step 16). Lubricants include, but are not limited to, naphtha, ISOPAR-G and ISOPAR-H, available from Exxon Corporation. According to the illustrative embodiment, the blended resin paste has a lubricant level from between about eight and twenty-five percent by weight. The paste may be subject to RGD treatment rather than or in addition to the resin (step 20). The blended resin is compressed in a preform mold at low pressure (typically less than 1000 PSI) into a preformed paste billet having a desired shape. Preform molds of a variety of shapes and sizes, and having both divided and undivided chambers, may be employed to mold the paste into a preformed billet. The volume of the resin typically reduces by one third from an original volume. Billet forming processes are well known in the art. It is also well known in the art that varying the lubricant level in the PTFE varies the porosity of the subsequently formed prosthesis. The billet may be subject to RGD treatment (step 22) in some embodiments.

A ram-type extruder, extrudes the preformed billet through a die having a selected cross-section (step 24). The preformed paste billet is extruded to a reduction ratio of between approximately 50:1 and 600:1. Typically, extrusion pressures between approximately 6000 PSI and 10,000 PSI are applied. The extrudate may be subject to RGD treatment in some embodiments (step 26). Optionally, the extrudate may be calendered into substantially flat stock. Subsequent to extrusion, and optionally calendering, the extrudate 18 is dried to remove the organic lubricant (step 28). The dried extrudate may be subject to RGD treatment (step 30). The dried extrudate is then stretched and/or expanded at least one time, preferably bilaterally and at elevated temperatures (step 32). In the case of PTFE, this results in the material taking on a microstructure characterized by elongated nodes interconnected by fibrils. Typically, the nodes orient with their elongated axis perpendicular to directions of stretch. The expanded extrudate may be subject to RGD treatment (step 34). Following stretching, the expanded extrudate is sintered by heating it to a temperature above its crystalline melting point while maintained in its stretched condition to produce a sintered extrudate (step 36). Sintering "locks-in" the microstructure of the substrate. The sintered extrudate may then be combined with other layers of treated or untreated polymers to create a multilayer substrate (step 38).

Sintered extrudates manufactured in this manner have wide ranging applications, such as devices for in vivo implantation, prostheses intended for placement or implantation to supplement or replace a segment of a natural biological blood vessel, and supports for tissue repair, reinforcement or augmentation. Specific products include but are not limited to heart valves, sutures, vascular access devices, vascular grafts, shunts and catheters. Other products include single and multilayered membranes. Multilayered membranes containing regions of selective porosity and chemistry are useful in the medical diagnostic and the filtration industries. For example, some clinical diagnostic test strips contain multilayer membranes with selective binding sites in each layer to capture analytes from blood, serum, and the like, when the test liquid is flowing through it. Fabricating such test strips using this technology results in a greater degree of chemical functionalities and/or binding sites resulting in improved signal to noise (i.e., greater selectivity and sensitivity), as well as, desirable permeability characteristics for liquid flow through the membrane. Both of which eliminate the need to laminate various layers with different properties. Filters are often made using multilayered laminates of different pore size. Filtration articles made from this technology provide a monolithic filter with inherent selective pore sizes and desired permeability characteristics rather than those created through lamination.

As discussed above, it is sometimes desirable to fabricate implantable devices with regions of varying porosity and/or chemistry characteristics. By way of example, it is sometimes desirable to encourage tissue in-growth to anchor an implant. In that case, a tissue contacting surface having sufficient porosity for enabling in-growth is required. Alternatively, it is not desirable for arterial grafts to become thrombosed. Accordingly, in those applications a less porous surface region is desirable. In other applications, it is desirable for an implant to be removeably anchored into position. Thus, in those applications it is desirable to have zones of increased porosity to encourage tissue in-growth, along with zones of reduced porosity to enable removeability.

For embodiments in which resins or pastes are RGD treated, devices embodying features of the invention are, by way of example, fabricated using preform molds of varying structures. The preform molds may be compartmentalized or unstructured in nature. Some suitable preform molds are described in more detail below. Preformed billets fabricated, according to the illustrative methods of the invention, from RGD treated paste or paste formed from RGD treated resin (herein after "treated paste") can be formed into substrates having tailored porosity, permeability, and/or chemistry characteristics. According to one embodiment, such substrates/devices fabricated in accord with the illustrative methods of the invention have regions of selected porosity, permeability, and/or chemistry. According to a further embodiment, such devices also have porosity, permeability, and/or chemistry gradients wherein, the porosity of the device varies from region to region in either a discrete or continuous manner.

According to an illustrative embodiment, a plurality of RGD treated pastes (i.e. RGD treated pastes or pastes formed from RGD treated resins) are combined in a selected manner in a preform mold to yield regions having differing porosity and chemistry characteristics. By way of example, pastes having been RGD treated differently can be layered in a preform mold to yield a preformed billet capable of being extruded into a substrate having a porosity gradient continuously changing over one or more regions. Alternatively, preform molds can include a plurality of compartments in which differently pretreated pastes are compressed to provide a preformed billet capable of being extruded into a substrate having a porosity gradient, wherein the substrate porosity changes discretely over regions of the structure previously defined by the preform mold compartments. Substrate chemistries and permeabilities can be similarly varied.

To further illustrate advantages of the invention, applicants performed several controlled experiments. The apparatus, methods and results of those experiments will now be discussed.

Figure 2:
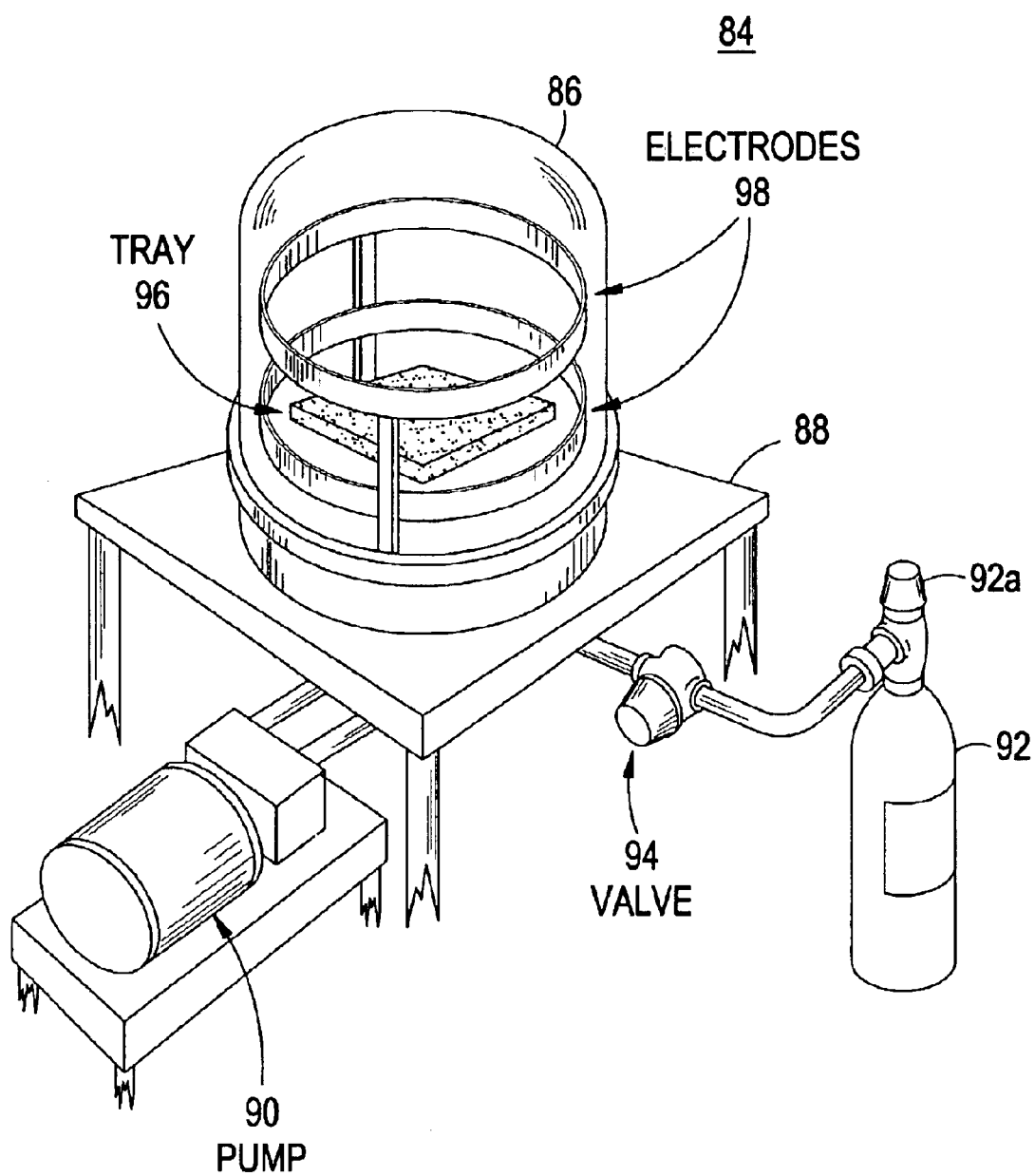
FIG. 2 is an exemplary system for plasma glow discharge treating polymeric materials in accord with an illustrative embodiment of the invention.

FIG. 2 depicts an apparatus 84 utilized in performing the illustrative experiments. The apparatus 84 includes a bell jar plasma reactor 86, a table 88 for supporting the reactor 86, a vacuum pump 90 for evacuating the reactor 86, an oxygen gas supply 92 for introducing oxygen (a non-polymer forming gas) into the evacuated reactor 86 by way of regulator 92a, and a bleed valve 94 for introducing air into the reactor 86 to bring the reactor 86 back to atmospheric pressure. A sample tray 96 holds the fluoropolymer material to be treated. The reactor 86 includes two electrodes 98 for subjecting the contents of the sample tray 96 to a glow discharge power. As configured, the apparatus 84 applies a RGD plasma activation treatment to fluoropolymer materials placed in the sample tray 96. However, as skilled artisans will appreciate, other plasma radiation treatments, such as, plasma activation and plasma etching, may also be employed.

For experimentation, a PTFE resin (Fluon CD-123 obtained from ICI Americas) was loaded onto the sample tray 96 and placed into the bell jar plasma reactor 86 as shown in FIG. 2. The vacuum pump 90 was employed to pump the pressure down to 20 mtorr. The oxygen gas supply 92 provided a non-polymer forming gas (e.g., oxygen) by way of the regulator 92a, at a flow rate sufficient to sustain a pressure of 100 mtorr. The electrodes 98 subjected the resin to a glow discharge power of 100 watts for 5 minutes. At the end of the 5 minutes, the bleed valve 94 was used to introduce air to bring the reactor 86 back to atmospheric pressure.

The RGD treated resin was blended with ISOPAR-H odorless solvent (produced by Exxon Corporation) as an extrusion aid at a level of 16% by weight per pound of resin. For control purposes, untreated (virgin) PTFE resin was also blended with ISOPAR-H odorless solvent as an extrusion aid at a level of 16% by weight per pound of resin in a manner identical to the treated resin.

FIG. 3 shows a perspective view of a preform mold 100 for fabricating a preformed billet having a tubular configuration. The preform mold 100 includes an outer wall 102 and a core rod 104. The outer wall 102 and the core rod 104 define a region 106. PTFE paste is poured into the region 106 and compressed into a preformed billet having a tubular configuration.

EXAMPLE 1

The RGD pretreated paste was poured into the region 106 of the preform cylinder mold 100 and compressed under a pressure of 300 PSI to produce a dense preformed tubular billet. The preformed billet was then placed into a ram extruder and extruded into a 6 mm ID×7 mm OD tube, at a reduction ratio of about 149:1 in cross-sectional area from billet to extruded tube. The volatile extrusion aid was removed by drying in a heated oven prior to stretching.

EXAMPLE 2

Untreated paste was poured into the region 106 of the preform cylinder mold 100 and compressed under a pressure of 300 PSI to produce a dense preformed tubular billet. The preformed billet was then placed into a ram extruder and extruded into a 6 mm ID×7 mm OD tube, at a reduction ratio of about 149:1 in cross-sectional area from billet to extruded tube. The volatile extrusion aid was removed by drying in a heated oven prior to stretching.

EXAMPLE 3

FIG. 4A is a perspective view of a cylindrical preform mold 110. The mold 110 includes concentric separating cylinders 112 and 114. The spacing vanes 118a and 118b space the cylinder 112 apart from an outer wall 116. The spacing vanes 120a and 120b space the cylinder 114 apart from the cylinder 112. A core rod cylinder 122 fits over a core rod of the preform mold 110 and aligns the cylinders 112 and 114 in the preform mold 110 during pouring.

The inner region 126 of preform mold 110 was filled with the untreated paste and the outer region 124 was filled with the RGD pretreated paste. FIG. 4B shows a longitudinal cross-sectional view of the filled mold 200 taken along line 4B—4B. More particularly, FIG. 4B shows the outer layer 124 formed from the untreated paste, the cylinder 112, the inner layer 126 formed from the RGD pretreated paste, and the core rod 122. The cylinder 112 was removed after pouring was completed, and a preformed billet was fabricated by compacting the layered mass under a compression pressure of 300 PSI, to produce a dense preformed billet having a concentric cylinder structure. The preformed billet was then placed into a ram extruder and extruded into a 6 mm ID and 7 mm OD tube, at a reduction ratio of 149:1 in cross-sectional area from preform to extruded tube.

EXAMPLE 4

FIG. 5 is a perspective view of another alternative preform mold 130. As shown in FIG. 5, the fixture 130 does not have a core rod, but instead employs a stainless steel sleeve 132. The stainless steel sleeve 132 fits concentrically within a cylinder 134, thus forming an inner region 136 separated from an outer region 138. The RGD pretreated paste was poured into the inner region 136 and the untreated paste was poured into the outer region 138. The cross-sectional shape of the stainless steel sleeve 132 was chosen such that the inner layer 136 of paste is exposed to the outside wall 134 at regions 140 and 142. The regions 140 and 142 form an external surface having a similar composition to the internal region 136. The sleeve 132 was removed after pouring was completed, and a preformed billet, was fabricated by compacting the layered mass under a compression pressure of 300 PSI, to produce a dense preformed billet. The preformed billet was then placed into a ram extruder and extruded into a 3.5 mm OD solid rod like structure, at a reduction ratio of 300:1 in cross-sectional area from preform to extruded rod.

Figure 6:
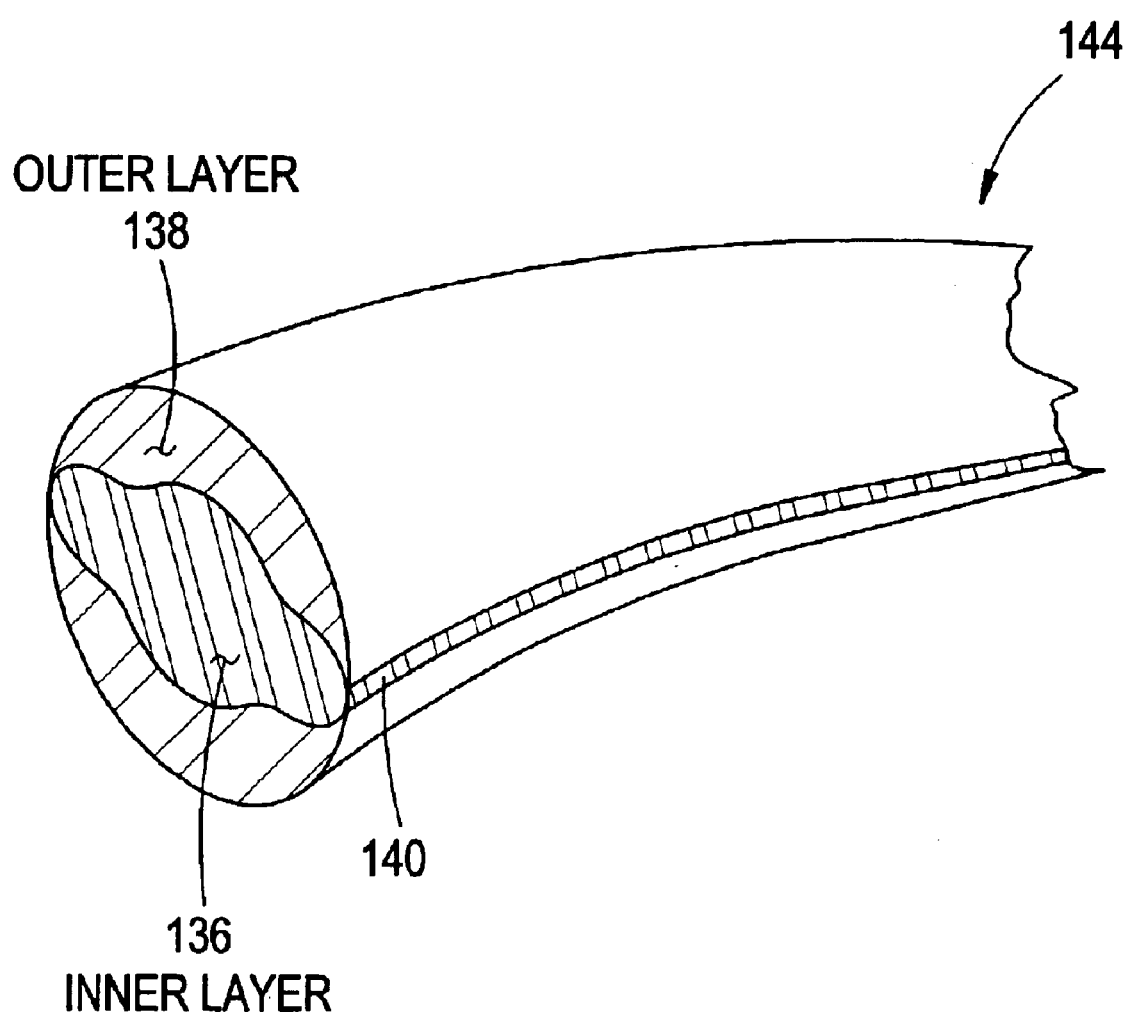
FIG. 6 is an extruded article formed from a billet fabricated with the illustrative mold of FIG. 5.

FIG. 6 is a cross-sectional perspective view of an extruded article 144 fabricated from the mold 130 of FIG. 5. The article 144 includes an inner layer 136 formed from the RGD pretreated paste, and an outer layer 138 formed from the untreated paste. The article 144 also includes an outer longitudinally extending surface region 140 having a similar composition to the inner layer 136.

Extrudate from each of the above examples was cut to 15" lengths and stretched to 45" final lengths using the methods disclosed in U.S. Pat. No. 5,474,824. TABLE 1 below provides several measured physical properties of the stretched extrudates. TABLE 2 illustrates changes in substrate chemistries resulting from the methods of the invention.

TABLE 1

| Sample | Pore Size (microns) | Water Entry Pressure (mm Hg) | Radial Burst Pressure (PSI) | Suture Retention (lbf) |
| --- | --- | --- | --- | --- |
| Ex. 1 | 150 | 100 | 60 | 1.05 |
| Ex. 2 | 20 | 280 | 58 | 0.61 |

TABLE 1-continued

| Sample | Pore Size (microns) | Water Entry Pressure (mm Hg) | Radial Burst Pressure (PSI) | Suture Retention (lbf) |
|---|---|---|---|---|
| Ex. 3 | 20 IN/150 OUT | 330 | 78 | 1.13 |
| Ex. 4 | 150 IN/20 OUT | N/A | N/A | |

TABLE 2

| SAMPLE | ATOMIC CONCENTRATION | | |
|---|---|---|---|
| | Carbon | Fluorine | Oxygen |
| Nontreated Control | | | |
| Inside surface | 30.6 | 69.4 | |
| Outside surface | 31.6 | 68.4 | |
| Plasma Treated Outside Surface | | | |
| Inside surface | 30.4 | 69.6 | |
| Outside surface | 33.4 | 65.2 | 1.4 |

As can be seen in TABLE 1, the pore size of the material formed from the RGD pretreated paste of Example 1 is significantly larger than the pore size of the material formed from the untreated paste of Example 2. Additionally, the water entry pressure is lower, the radial burst pressure is higher, and the suture retention is better for the RGD treated material of Example 1 than for the untreated material of Example 2. Additional information can be gleaned by examining scanning electron micrographs of the materials formed in the above-discussed illustrative examples.

Figure 7:
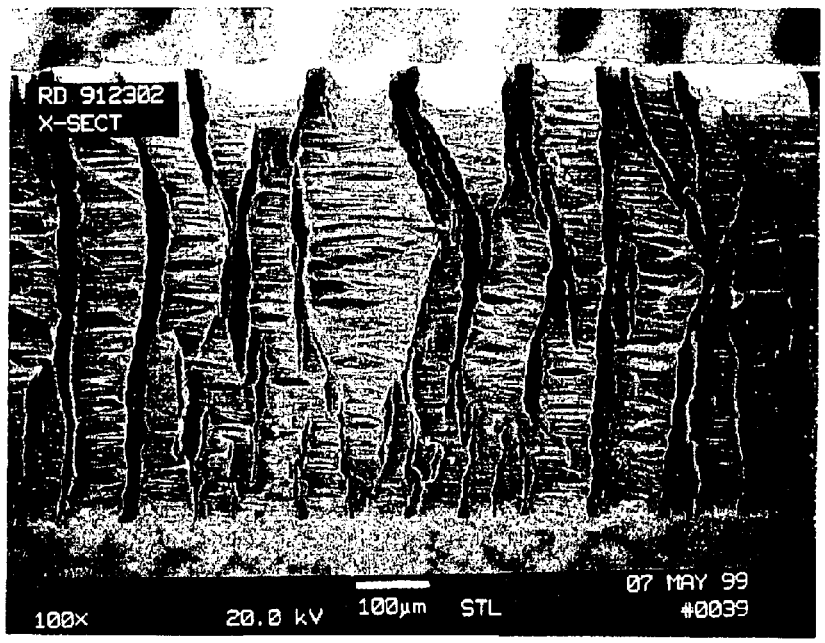
FIG. 7 is a cross-sectional scanning electron micrograph of a substrate fabricated using the preform mold of FIG. 3 and employing a plasma glow discharge treatment according to an illustrative embodiment of the invention.

FIG. 7 is a scanning electron micrograph showing the node and fibril structure of a substrate prepared according to Example 1, using RGD treated PTFE resin. As shown at 150, the average distance between nodes (internodal distance) is about 150 microns.

Figure 8:
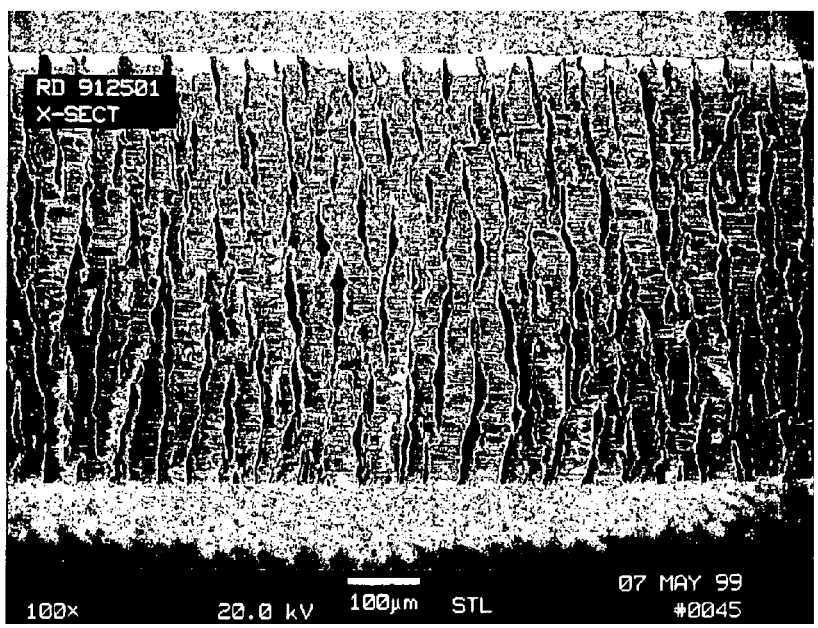
FIG. 8 is a cross-sectional scanning electron micrograph of a substrate fabricated using the preform mold of FIG. 3 and employing untreated resin.

FIG. 8 is a scanning electron micrograph showing the node and fibril structure of a substrate prepared according to Example 2, using untreated PTFE resin. The average distance 152 between nodes is about 20 microns. As can be seen from FIGS. 7 and 8, the average nodal distance is more than seven times greater in the substrate formed from the RGD treated PTFE resin. Thus, the substrate formed from the RGD treated PTFE resin of Example 1 (FIG. 7) is substantially more porous and has a lower fibril density than the substrate formed from the untreated PTFE resin of Example 2 (FIG. 8).

Standard surface analysis techniques were used to measure the chemistry characteristics of the substrate of Example 2. As shown in TABLE 2, the outer surface 151 (FIG. 8) and the inner surface 153 of the untreated control substrate also have substantially identical carbon concentrations and flourine concentrations. Additionally, the untreated control substrate has virtually no oxygen concentration.

Figure 9:
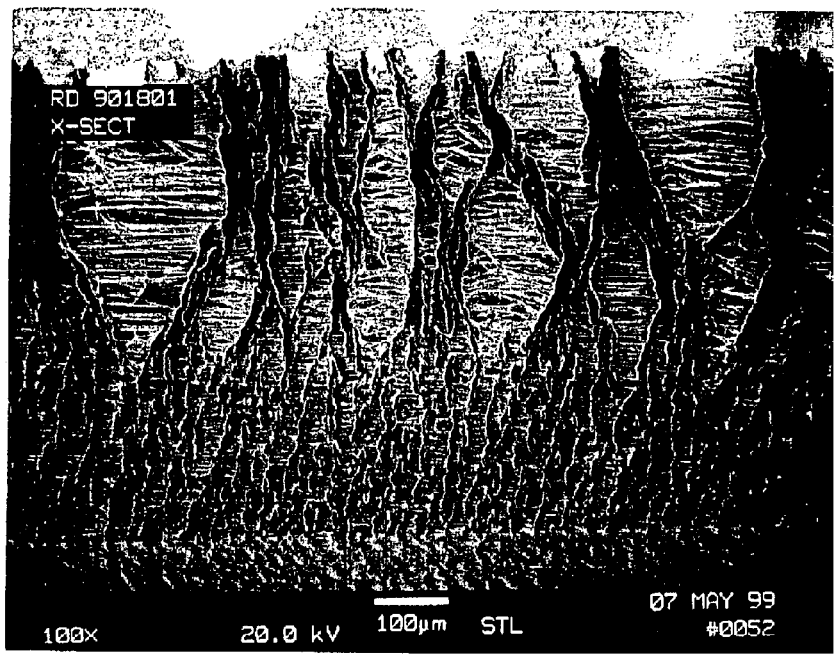
FIG. 9 is a cross-sectional scanning electron micrograph of a substrate fabricated using the preform mold of FIG. 4A and employing a plasma glow discharge treatment according to an illustrative embodiment of the invention.

FIG. 9 is a scanning electron micrograph showing the node and fibril structure of a substrate prepared according to Example 3, using RGD treated PTFE resin in an outer region 154 and untreated PTFE resin in an inner region 156. The layered preformed billet results in a structure having a differential porosity. In the RGD treated outer region 154, the average distance 158 between nodes is about 150 microns. Whereas, in the untreated inner region 156 the average distance 160 between nodes is about 20 microns. The scanning electron micrograph of FIG. 9 also illustrates the formation of a discrete border 155 between the relatively porous region 154 and the relatively non-porous region 156. (Note the separation between 154 and 156 has been added to the electron micrograph).

Once again, standard surface analysis techniques were used to evaluate the chemistry characteristics of the substrate prepared according to Example 3. As shown in TABLE 2, the untreated inner surface region 156 has substantially identical atomic concentrations of carbon and fluorine as the control substrate of Example 2. However, the outer region 154 formed from the treated resin has a higher concentration of carbon, a lower concentration of fluorine and includes oxygen. Thus, the processes of the invention also provide tailored chemistry characteristics.

Figure 10:
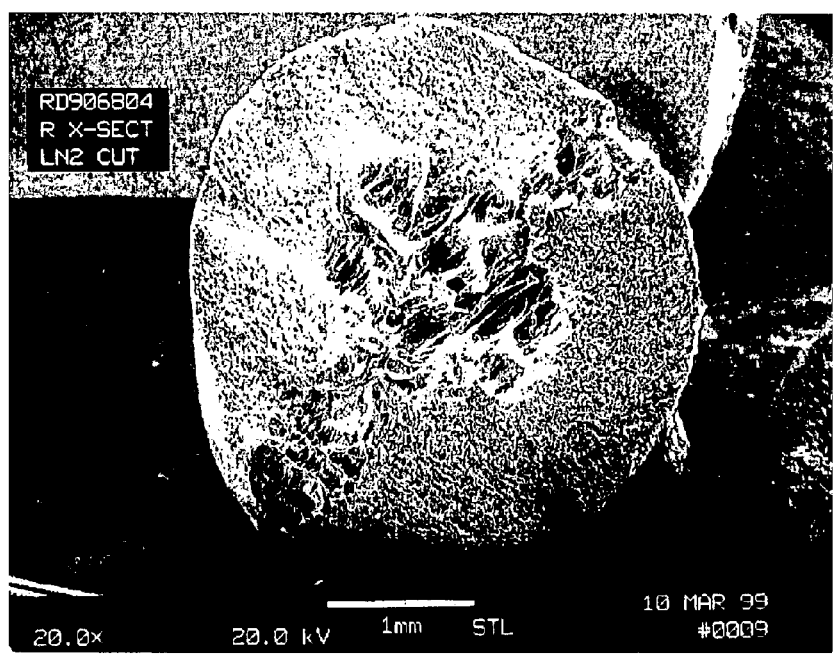
FIG. 10 is a cross-sectional scanning electron micrograph of a substrate fabricated using the preform mold of FIG. 5 and employing a plasma glow discharge treatment according to an illustrative embodiment of the invention.

FIG. 10 is a scanning electron micrograph showing the node and fibril structure of the material prepared according to Example 4, using RGD treated PTFE resin in an inner region 158 and untreated PTFE resin in an outer region 160. In the untreated outer region 160, the average distance between nodes is about 20 microns. However, in the RGD treated inner region 158, the average distance between nodes is about 150 microns. The unique shape of mold 10 results in an extruded article, as shown in FIG. 10, that has external regions 162 and 164 (also shown at 140 and 142 in FIG. 6) which extend along an external length of the extrudate 140 and contain RGD treated portions.

As shown in the scanning electron micrographs of FIGS. 7, 9 and 10, the plasma glow discharge treatment methods of the invention enable tailoring of a polymer substrate's bulk characteristics, such as porosity, node size and fibril density. Also, as shown in FIGS. 9 and 10, the illustrative embodiment of the invention also provides polymer substrates having configurable regions with selected bulk characteristics. As shown in TABLE 2, the methods of the invention also enabling tailoring of a polymer substrate's bulk chemistry characteristics. Moreover, unlike prior methods, which required treating the entire substrate, the methods of the invention enable altering the chemistry characteristics of selected substrate regions. According to one embodiment of the invention, a polymeric substrate can be fabricated having any number of regions, with each region having any desirable node size, fibril density, porosity, or chemistry characteristic.

Figure 11:
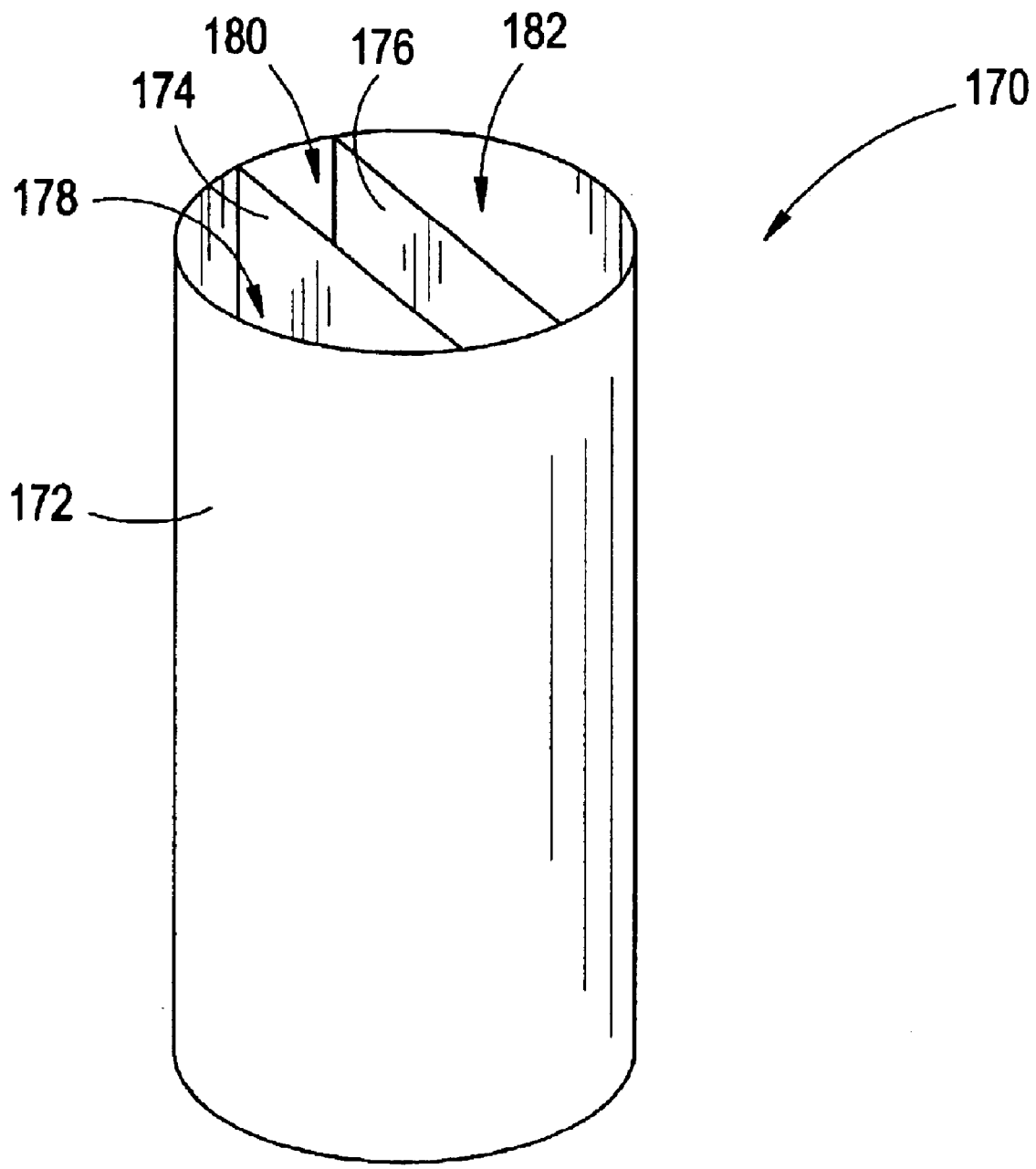
FIG. 11 is a perspective view of another alternative preform mold employed in conjunction with an illustrative embodiment of the invention.

FIG. 11 depicts an alternative preform mold 170 from which preformed billets embodying features of the invention can be fabricated. The preform mold 170 includes an outermost wall 172 which defines a cylindrical space. The separating walls 174 and 176 subdivide the cylindrical space into regions 178, 180 and 182. While, the mold 170 is depicted with two separating walls 174 and 176, one alternative embodiment includes only one separating wall, while other alternate embodiments include more than two separating walls.

By filling the regions 178, 180 and 182 with PTFE pastes RGD treated in different manners, a billet can be fabricated having axially extending layers wherein each layer has different bulk characteristics. Accordingly, a resulting extrudate also has axially extending layers with different bulk characteristics. In an alternative embodiment, the preformed billet is extruded and then calendered between rollers into a flat stock, with each of the layers of the flat stock having a porosity characteristic related to the particular pretreated paste used to form the layer. Regardless of whether the billet is calendered, according to the illustrated embodiment of the invention, it is subsequently dried, stretched/expanded and sintered to lock in the characteristic microstructure.

Figure 12:
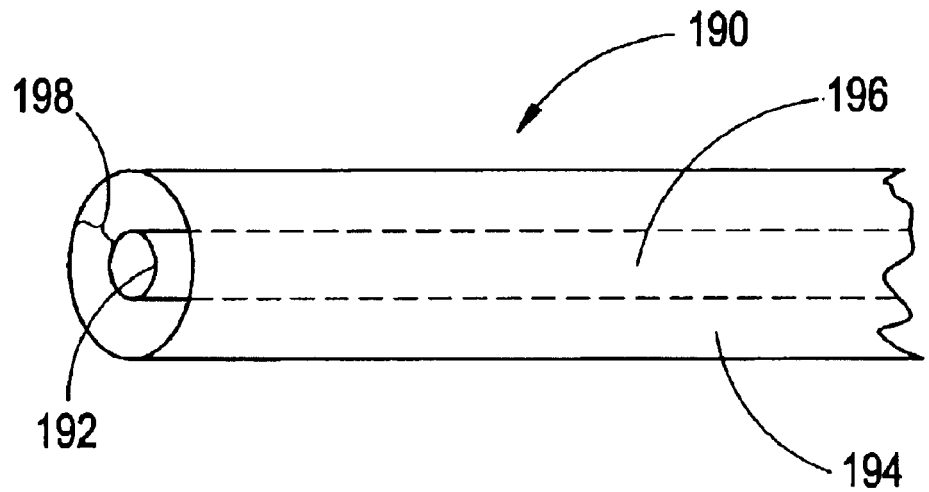
FIG. 12 depicts an implantable prosthesis constructed using the preform mold of FIG. 3.

FIG. 12 shows an implantable prosthesis 190 formed according to methods of the invention using a preform mold such as that shown at 100 in FIG. 3. The prosthesis 190 is tubular in nature and suitable for implantation as a vascular graft. The prosthesis 190 has an inner wall surface 192 and an outer wall surface 194. The inner wall surface 192 defines an axially directed passageway 196, through which blood can flow. The inner wall surface 192 and the outer wall surface 194 together define a wall region 198. According to one aspect of the invention, the vascular prosthesis 190 is formed from resins, pastes, billets or unexpanded extrudates having previously been treated with plasma radiation to provide a tailored porosity characteristic. According to one feature of the illustrated embodiment, the wall region 198 has a tailored porosity gradient, which continuously varies from least porous at the inner wall surface 192 to most porous at the outer wall surface 194. Similarly, the wall region 198 also has a chemistry gradient, which continuously varies from having essentially no concentration of oxygen atoms at the inner wall surface 192 to having a higher concentration of oxygen atoms at the outer wall surface 194.

According to a further feature of the illustrated embodiment, the outer wall surface 194 of the vascular prosthesis 190, has a porosity which is compatible with and serves as a micro-scaffolding structure for the growth of connective tissue. In contrast, the inner wall surface 192 has a smaller pore structure, optimized for attachment of a neointima for reconstituting a natural biological flow surface at the interior of the vessel. The modulation region 198 blocks the direct or immediate transmission of hydrostatic pressure or fluid migration through the thickness dimension between inner wall 192 and the outer wall 194, and prevents through-growth of tissue, allowing a stratification of tissue layers to redevelop over time in a more natural fashion after the prosthesis 190 is implanted.

In this way, the prosthesis 190 provides a structure wherein tissue in-growth can occur at the outer wall surface 194 to anchor the prosthesis 190 in place, and blood flow can occur along the inner wall surface 192, without seepage, through region 198.

Figure 13:
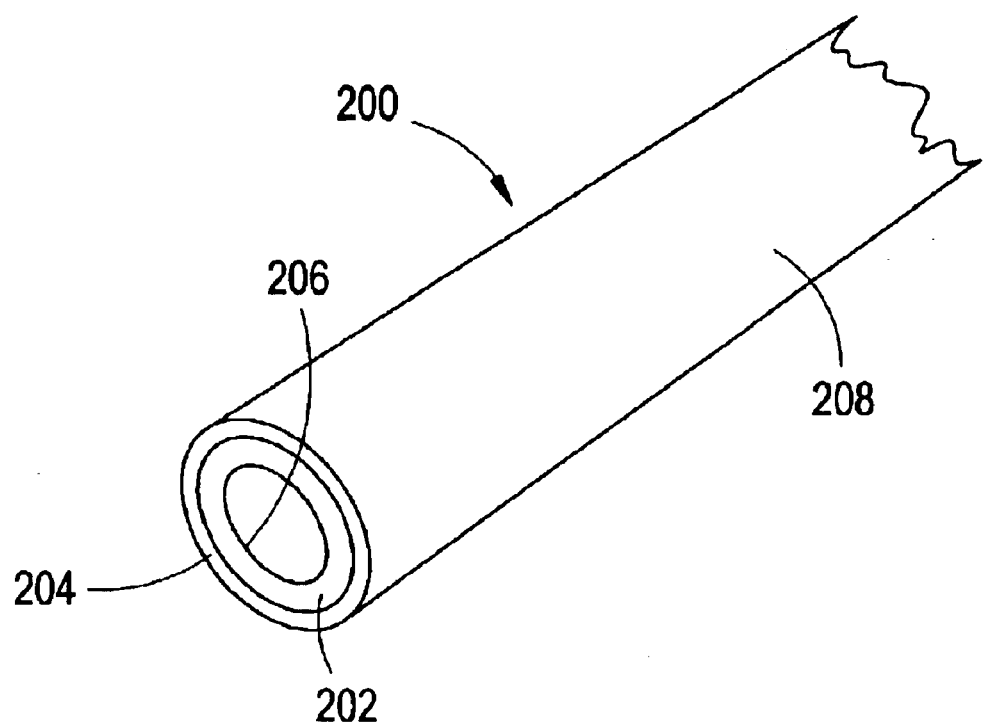
FIG. 13 depicts a two layer tubular billet formed using the preform mold of FIG. 4A.

FIG. 13 is a perspective view of a two-layer tubular preformed billet 200 fabricated with plasma treated PTFE components according to an illustrative embodiment of the invention. According to the illustrative embodiment, the preformed billet 200 is fabricated using a preform mold such as the preform mold 110 depicted in FIG. 4A. The preformed billet 200 includes a radial inner portion 202, a radial outer portion 204, an innermost wall 206 and an outermost wall 208. A feature of the preformed billet 200 is that the radial portions 202 and 204 are formed by pouring differently RGD treated PTFE pastes into each portion 202 and 204. In an alternative embodiment, the radial portions 202 and 204 are formed by pouring a RGD treated PTFE paste into one of portions 202 and 204 and pouring an untreated paste into the other of the portions 202 and 204.

Whereas the prosthesis 190 of FIG. 12 provides a wall portion 198 having a continuous porosity/chemistry gradient between the outer wall surface 194 and the inner wall surface 192, prostheses fabricated from billet 200 provide a wall structure having a first discrete porosity/chemistry characteristic in the outer radial region 204 and a second discrete porosity/chemistry characteristic in the inner radial region 202. By tailoring the porosity in the region 202 to be less than the porosity in the outer radial region 204, the prosthesis 200 provides a seepage resistant flow channel along the inner wall 206, while fostering improved cellular in-growth along the outer surface 208.

In addition to the radial extending continuous porosity/chemistry gradient of the prosthesis 190 and the discrete radial extending porosity/chemistry gradient of the prosthesis 200, a plethora of other porosity/chemistry gradients may be established using the methods of the invention. By way of example, porosity/chemistry gradients may vary discretely over selected regions and continuously over other regions. Additionally, porosity/chemistry gradients may vary in both radial and axial directions.

FIG. 14 is a perspective view of an alternative implantable prosthesis 230 fabricated in accord with methods of the invention. The prosthesis 230 includes an outermost wall surface 232 and an inner most wall surface 234. The innermost wall surface 234 defines an axially directed channel 236. The innermost wall surface 234 together with the outermost wall surface 232 defines a wall region 238 formed there between. According to one embodiment, the prosthesis 230 includes discrete axially extending regions 210, 242 and 244 having tailored porosity and chemistry characteristics, formed according to methods of the invention. By way of example, regions 240, 242 and 244 can be regions of increased porosity with respect to the remainder of the prosthesis 230, thus providing regions felicitating tissue in-growth. The regions 240, 242 and 244 can extend uniformly radially between the concentric surfaces 232 and 234. Alternatively, regions 240, 242 and 244 can have individually tailored, continuous or discrete, porosity/chemistry gradients, as described with respect to FIGS. 12 and 13. Moreover, the porosity/chemistry gradients of the regions 240, 242, and 244 can vary in the axial and/or radial directions. Furthermore, the regions 246 and 248, can also have tailored porosity/chemistry gradients, which vary axially and/or radially. According to a further embodiment of the invention, the prosthesis 230 can be formed without the channel 234 and the regions 240, 242 and 244 can extend radially through the prosthesis 230.

FIG. 15 depicts an implantable prosthesis 250. The prosthesis 250 has an outermost wall surface 252 and optionally, an innermost wall surface 254. The optional innermost wall surface 254 defines an axially extending channel 256. The outermost wall surface 252 and the optional innermost wall surface 254 define a wall region 258 therebetween. According to one embodiment, the prosthesis 250 is used for tissue augmentation. As such, the prosthesis 250 includes discrete regions 260 having relatively high porosity characteristics to encourage tissue in-growth and anchoring. Additionally, plasma treatment to produce chemical moieties in specific regions can provide binding sites for covalent attachment of growth factors and biological species to encourage specific cell type and tissue in-growth. According to an alternative embodiment, axial distil internal surface regions 262 and 264 have increased porosity to encourage tissue in-growth at the distal ends anchor the prosthesis 250 in place. In one aspect, the increased porosity characteristics of the regions 262 and 264 are formed as a porosity gradient, decreasing from the inner surface 254 to the outer surface 252, in opposition to the porosity gradient discussed with respect to the region 198 of FIG. 12. In an alternative aspect, the regions 262 and 264 have discrete regions of tailored porosity, similar to region 202 of FIG. 13. As is the case of previously discussed structures, the porosity and chemistry characteristics illustrated in FIG. 15 are achievable by employing plasma radiation treated resin or paste and an undivided or a selectively divided preform mold, such as those depicted in FIGS. 3, 4A, 5 and 11.

Figure 16A:
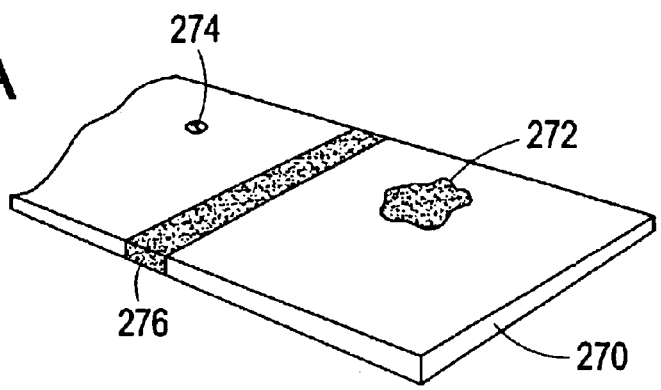
FIG. 16A depicts an illustrative flat stock material formed in accord with an illustrative embodiment of the invention and having exemplary discrete regions of selective porosity and chemistry characteristics.
Figure 16B:
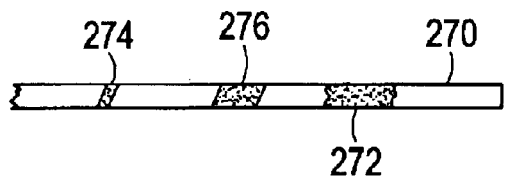
FIG. 16B is a side view of the flat stock material of FIG. 16A.
Figure 17:
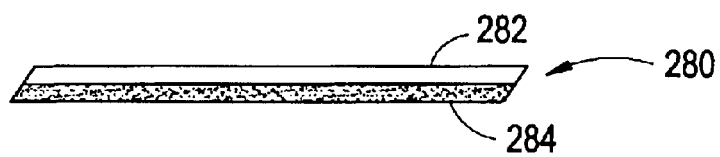
FIG. 17 depicts a side view of an alternative flat stock structure formed in accord with an illustrative embodiment of the invention.

FIGS. 16A, 16B and 17 depict flat stock structures, such as those employed for prosthetic patches. By way of example, FIG. 16A depicts a planar view of a prosthetic patch 270. That includes at least three different regions 272, 274 and 276, each having differing porosity and chemistry characteristics. More specifically, the region 274 illustrates an anchoring point for encouraging tissue in-growth. While it is desirable to adequately fasten the prosthetic patch 270, it also may be desirable to be able to remove the prosthesis 270. An anchoring point of limited size, such as the anchoring point 274, provides such a feature. As illustrated in the cross-sectional view of FIG. 16B, the anchoring point 274 can extend partially or completely through the prosthetic patch 270. According to one embodiment of the invention, the anchoring point 274 is fabricated by including an amount of RGD treated PTFE paste at a desired location in a preform mold, prior to extruding into a preformed billet or calendering into flat stock.

The prosthesis 270 also includes an illustrative banded region 276 having a tailored porosity/chemistry characteristic. According to one embodiment of the invention, the banded region 276 is formed by pouring an amount of RGD treated PTFE paste into an intermediate region of a preform mold and extruding, calendering, drying, expanding and sintering the resulting billet to yield the porosity characteristic illustrated by the banded region 276. As shown in FIG. 16B, the banded region 276 may extend uniformly through the stock 270, or may be graded to increase or decrease the porosity or vary the substrate chemistry in any direction.

The region 272 shows that illustrative methods of the invention provides patches of virtually any shape, either extending partially through the prosthesis 270, or as shown at 272 of FIG. 16B, extending all the way through the prosthesis 270.

FIG. 17 is a side view of an alternative prosthetic patch structure 280 formed according to another embodiment of the invention. The prosthetic patch 280 includes a first planar region 282 having first porosity/chemistry characteristics, and a second planar region 282 having second porosity/chemistry characteristics. According to the illustrative embodiment, the regions 282 and 284 are created by employing first and second differently RGD treated extruded billets, bonded together through sintering to form a single structure 280 having the regions 282 and 284. In an alternative embodiment, the prosthetic patch 280 is formed by employing two differently RGD treated PTFE resins or pastes, layered and then extruded, dried, expanded and sintered to form the single structure 280, with the regions 282 and 284.

Figure 18:
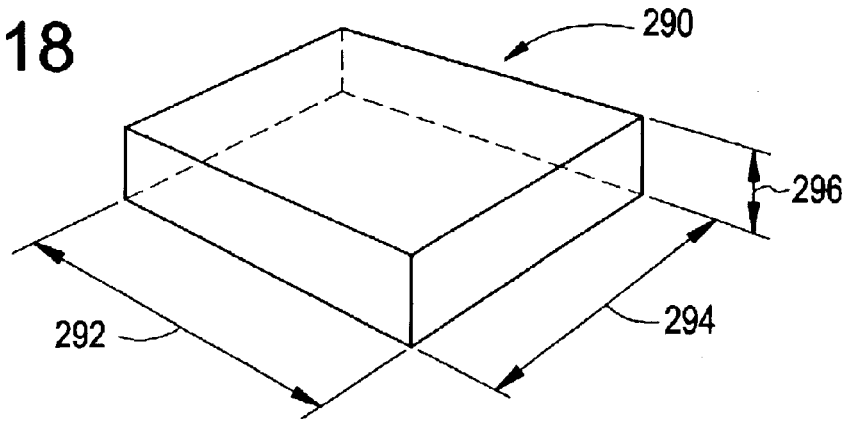
FIG. 18 is a perspective view of a substantially solid substrate formed in accord with an illustrative embodiment of the invention and having porosity and chemistry gradients varying in up to three dimensions.

FIG. 18 is a perspective view of a three-dimensional implantable prosthesis 290 formed in accordance with an illustrative embodiment of the invention. As will be appreciated by skilled artisans, examples of the prosthesis 290 include, but are not limited to, devices for in vivo implantation, implantable prosthetics for the delivery of bioactive materials, prosthetics intended for placement or implantation to supplement or replace a segment of a natural biological blood vessel, and implantable supports for tissue repair and reinforcement or augmentation. According to one embodiment, the prosthesis 290 is formed with a porosity gradient and chemistry characteristic varying, either discretely or continuously, along a length axis 292, a width axis 294, and/or height axis 296.

According to one embodiment of the invention, such porosity gradients and chemistry characteristics are achieved by combining a plurality of selectively RGD treated preformed billets. More specifically, a plurality of selectively RGD treated preformed billets are layered to form a selected porosity/chemistry gradient along any of axes 292, 294 and 296. The layered billets are then calendered or extruded, dried, expanded and sintered. Alternatively, a plurality of pretreated PTFE pastes or PTFE pastes formed from pretreated PTFE resin are combined in a selected manner in a preform mold. In one aspect, the preform mold is undivided, with the PTFE pastes distributed in a selected manner within the mold. Alternatively, the preform mold is compartmentalized along one or more axes, such as those depicted in FIGS. 4A, 5 and 11, to facilitate distribution of the pretreated PTFE paste. According to a further embodiment, billets so formed are extruded, dried, expanded and sintered. As shown in FIG. 18, products fabricated in accord with methods of the invention provide the ability for tailoring the porosity/chemistry characteristics of the prosthesis 290 in any desirable manner. As previously discussed, such an ability is quite advantageous for tailoring the tissue ingrowth, liquid seepage and biocompatability characteristics of prosthetic implants. Additionally, tailoring porosity and chemistry is also valuable in designing devices for in vivo delivery of bioactive materials. A further application is for the fabrication of improved single and multi-layered membranes for use in the medical diagnostics and the filtration industries.

The techniques of the present invention may be employed to create implantable prosthetic devices that are adapted for delivery bioactive materials. For example, vascular grafts with multiple lumens may be created using the techniques described herein. The physical structure components in such prosthetic devices is discussed in further in detail U.S. Pat. No. 5,411,550, entitled "Implantable Prosthetic Device for the Delivery of a Bioactive Material," the contents of which are incorporated herein by reference.

Figure 19:
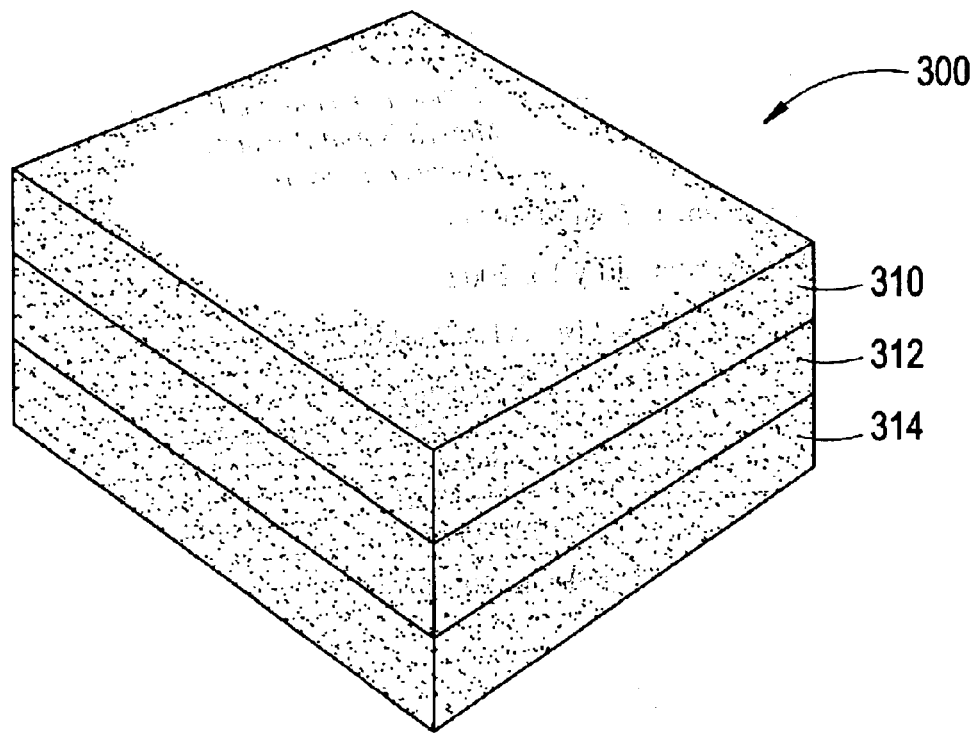
FIG. 19 depicts an example filtration device formed in accordance with an illustrative embodiment.

As mentioned above, the techniques described herein may be used to generate filters. FIG. 19 shows one example of a filtration device having layers 310, 312 and 314 that are formed using the above-described process as set forth in FIG. 1. Each of the layers 310, 312 and 314 may be formed by a polymer, such as PTFE, that has been subject to RGD treatment as described above. The RGD treatment may alter the permeability or porosity of the layers so as to produce the desired filtering effect. For example, Layer 310 may be formed from a resin that was subject to RGD treatment to have a high level of porosity. Layer 312 may be formed from a resin that was subject to RGD treatment to provide a moderate level of porosity. Layer 314 may be formed from a resin that was subject to RGD treatment to provide a low level of porosity. Thus, a fluid flows through the filter device 300 beginning with layer 310, each of the respective layers 310, 312 and 314 filters out and captures components at the fluid. The filtered fluid passes out of layer 314.

The filters need not be configured to vary as to porosity alone. Instead, the filter layers 310, 312 and 314 may vary as to permeability or may chemically vary so as to selectively bind to components in the fluid that is being filtered. The layers may vary from each other in any combination of porosity characteristics, permeability characteristics and chemical properties.

Those skilled in the art will appreciate that the filtration device 300 need not be a three layer structure but rather may be a single layer structure, two layer structure or even have greater than three layers. The illustration of a three layer structure in FIG. 19 is intended to be merely illustrative and limiting of the present invention. Moreover, the thickness of the layers may not be uniform and the geometry of the layer may vary dramatically from that depicted in FIG. 19.

Figure 20:
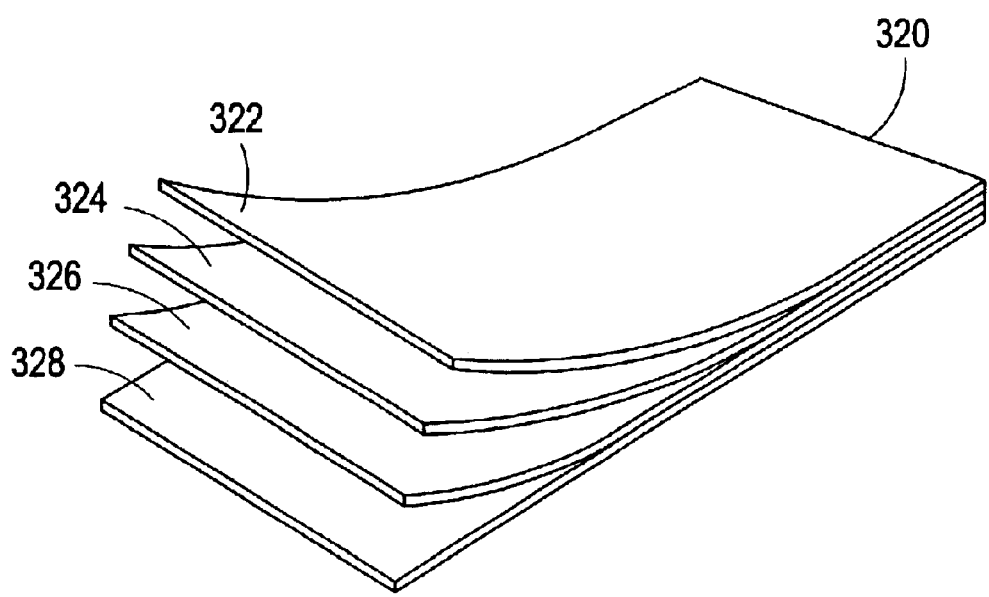
FIG. 20 depicts an example test strip formed in accordance with an illustrative embodiment.

The present invention may also be used to generate test strips. FIG. 20 depicts an example of a test strip 320 that is formed from four layers 322, 324, 326 and 328. Each of the layers constitutes a portion flatstock PTFE. The layers 322, 324, 326 and 328 may be configured so as to vary as to probability, porosity and chemical properties by applying RGD treatment, as described above. The layers 322, 324, 326 and 328 may be laminated together to form a test strip 320. For example, the test strip 320 may be designed to accept a sample of biological fluid to test for certain properties. The layers 322, 324, 326 and 328 may be configured so as to capture components of the biological fluid and bind to respective components in the biological fluid. The layers 322, 324, 326 and 328 may include reagents that interact with components of the biological fluid. As described above, the polymers used in the layers 322, 324, 326 and 328 may be subject to RGD treatment to alter the chemical properties so that certain bioactive agents may be attached to the polymers. Such a test strip 320 may be suitable for accepting blood samples and determining glucose levels for diabetic patients, for example.

Figure 21:
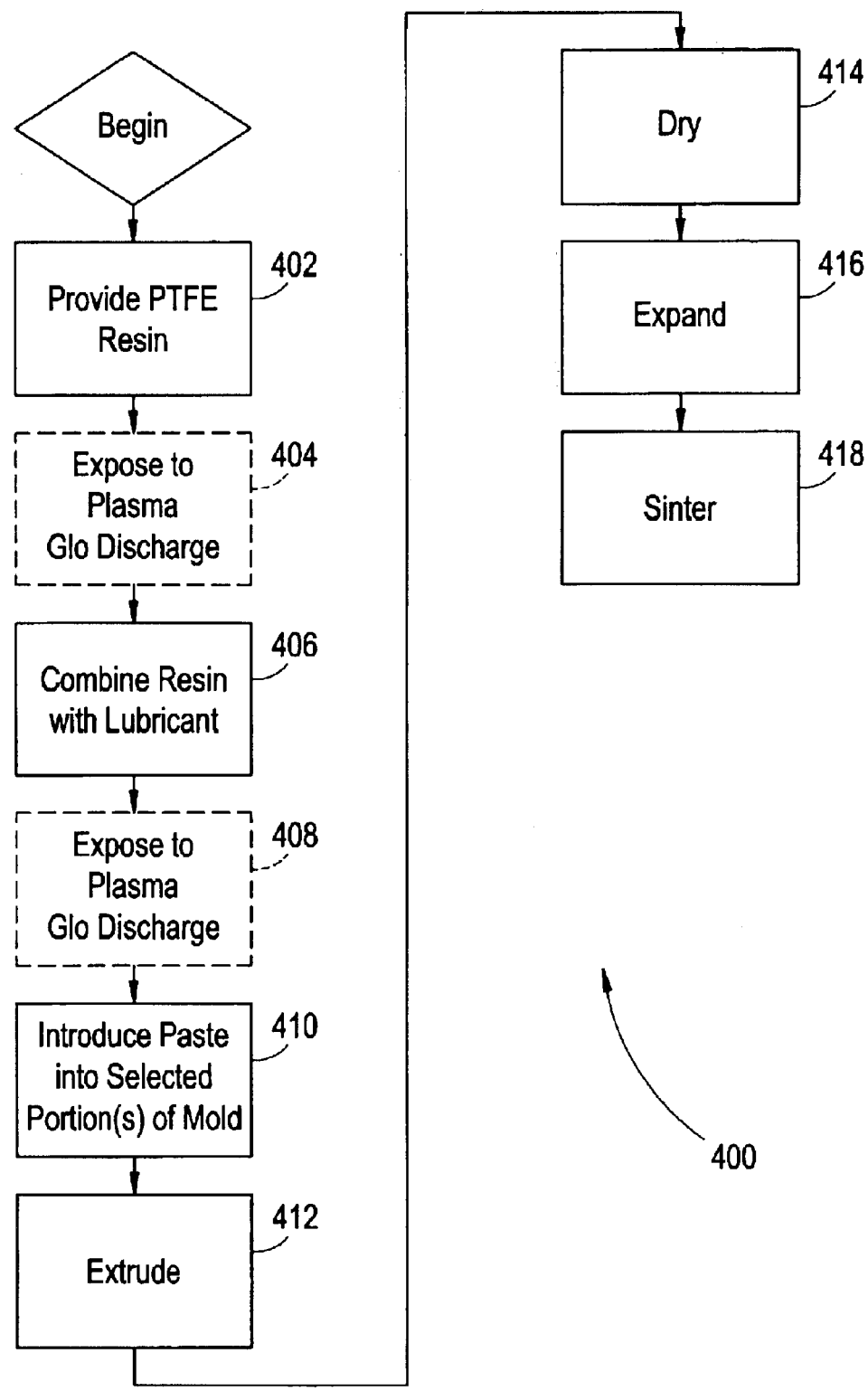
FIG. 21 is a flow chart depicting a process for fabricating polymeric substrates having tailored permeability, porosity and/or chemistry characteristics.

FIG. 21 is directed to fabricating devices having tailored porosity characteristics from PTFE resins or pastes that are plasma glow discharge pretreated in accord with methods of the invention. As shown at 402, the first step in the method of flowchart 400 is to provide a PTFE resin, such as Fiuon CD-123 available from ICI Americas. As shown at 404, the resin is then be exposed to a plasma glow discharge treatment, such as the RGD plasma activation treatment of Example 1, wherein the resin is exposed to a glow discharge power of 100 W for 5 minutes in an oxygen gas environment maintained at 10 mTorr. With the resin in particulate form, substantial surface treatment is achieved. These treated particles subsequently become imbedded into the microstructure of the fabricated devices and effect the porosity and chemistry characteristic s of the fabricated device in a calebratable fashion. As shown at 406, the pretreated resin is combined with an organic lubricant, such as ISOPAR-H odorless solvent, produced by Exxon Corporation, to form a pretreated paste. As disclosed in U.S. Pat. No. 5,433,909, entitled "Method of Making Controlled Porosity Expanded Polytetrafluoroethylene Products," the contents of which are herein incorporated by reference, the porosity characteristic of a fabricated device may be further tailored by controlling the amount of lubricant used. According to one embodiment of the invention, the lubricant level and the plasma glow discharge treatment process is varied in combination to achieve selectable porosity and chemistry characteristics. According to the illustrative embodiment, the organic lubricant is combined with the resin at a level of 16% by weight per pound of resin.

As shown at steps 410 through 418, subsequent to combining the RGD treated resin with the lubricant, the resulting PTFE paste is formed into a billet, extruded, dried, expanded/stretched and sintered, all according to methods well known in the art.

In an alternative embodiment of the invention, instead of RGD treating the resin at step 404, the resin is first combined with the of lubricant in step 406. The resulting paste is then plasma glow discharge treated in step 408, much in the same way that the PTFE resin was RGD treated in step 404. The dashed lines at steps 404 and 408 indicate that the plasma glow discharge treatment step can occur either at step 404 or at step 408, but preferably not at both.

Figure 22:
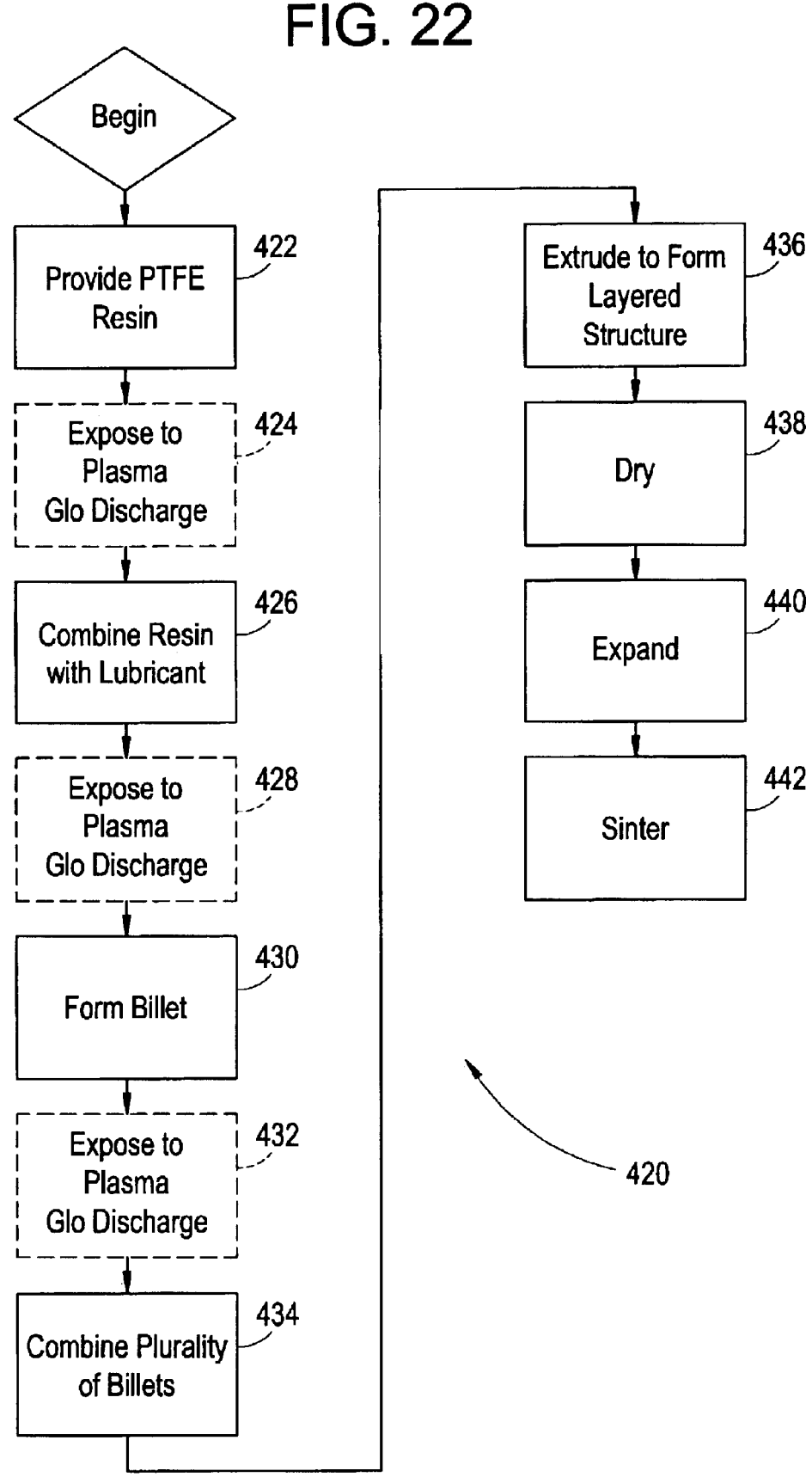
FIG. 22 is a flow chart depicting an alternative process for fabricating polymeric substrates having tailored permeability, porosity and/or chemistry characteristics.

FIG. 22 depicts a flowchart 420, illustrative an alternative method of the invention, for fabricating devices. Unlike the method 400, which is directed to combining a plurality of differently RGD treated resins or pastes to form a device having selected porosity and/or chemistry characteristics, the method 420 is directed to combining a plurality of preformed billets, fabricated in accord with the methods of the invention, to produce devices having selected porosity and/or chemistry characteristics. As shown at 422, the first step is to provide a suitable resin, such as ISOPAR-H odorless resin available from Exxon Corporation. As shown at 424, according to one embodiment the resin is pretreated with a plasma glow discharge treatment as discussed above. Next, at step 426, the pretreated resin is combined with a selected amount of lubricant. In an alternative embodiment, the resultant paste is pretreated at step 428. Regardless of whether the resin or the paste is pretreated, the resultant pretreated paste is compressed into a preformed billet at step 420. According to an alternative embodiment, instead of RGD treating the resin or the paste, the preformed billet is RGD treated at step 422. As shown at steps 434 and 436, and as previously, according to one embodiment, devices having tailored porosity and chemistry characteristics are formed by combining/layering a plurality of differently RGD treated billets, optionally, also having different lubrication levels, and then extruding or calendering the combination billet in a well known manner. As shown in steps 438–442, the resulting extrudate is then dried, expanded/stretched and sintered to form the desired structure. Once again, the dashed lines of blocks 424, 428 and 432 indicate the several stages at which the plasma glow discharge treatment of the invention can occur.

Figure 23:
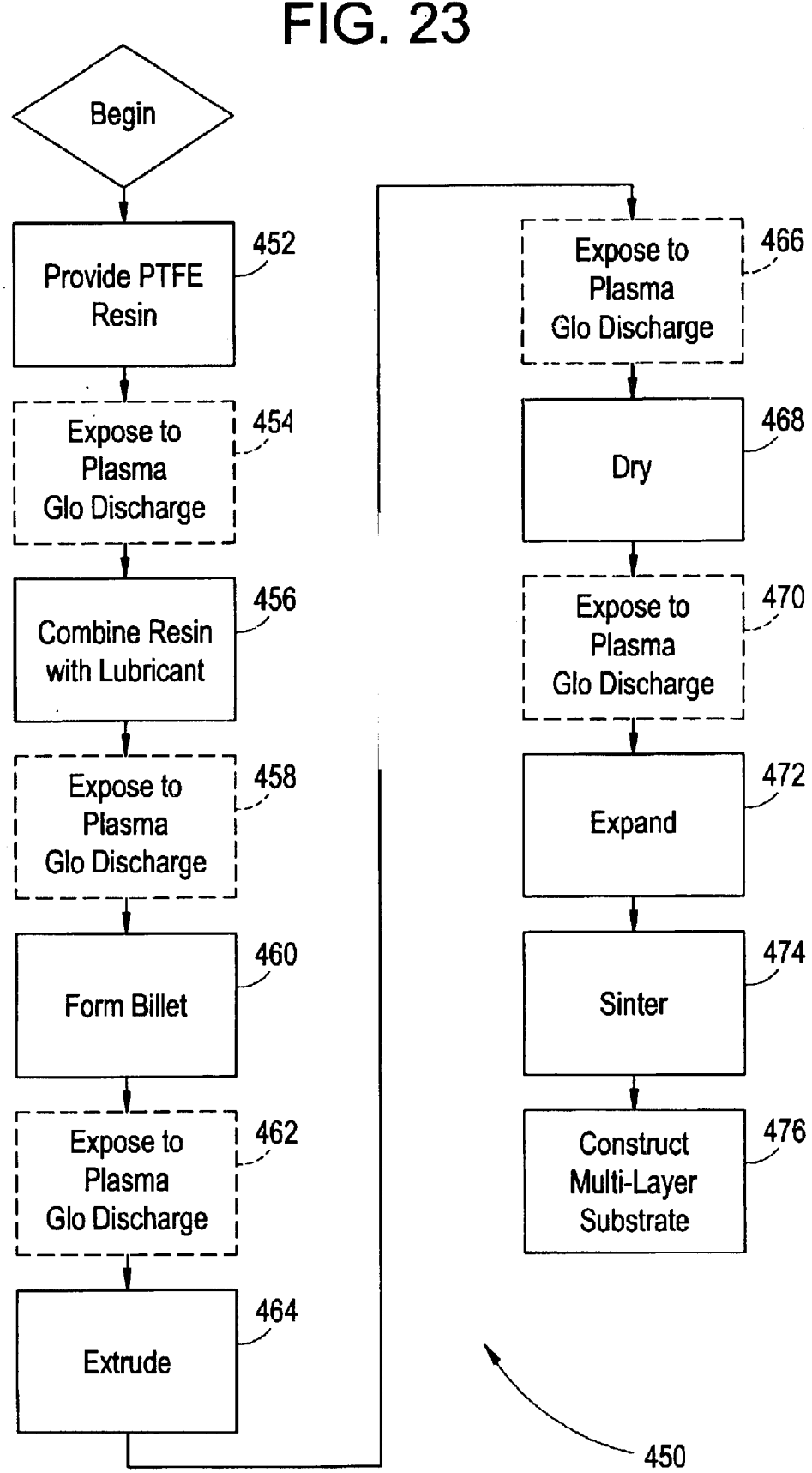
FIG. 23 is a flow chart depicting another alternative process for fabricating polymeric substrates having tailor permeability, porosity and/or chemistry characteristics.

FIG. 23 depicts a flowchart 450 illustrative of another alternative method of the invention. Unlike the method of FIG. 21, which is directed to using a plurality of differently RGD treated PTFE resins and pastes to achieve a desired porosity gradient, or the method of FIG. 22, which is directed to using a plurality of differently RGD treated preformed billets to achieve a desired porosity gradient, the method 450 of FIG. 23 is directed to using a plurality of expanded, sintered extrudates to achieve a desired porosity gradient. U.S. Pat. No. 5,824,050, entitled "Prosthesis With In-Wall Modulation," the contents of which are hereby incorporated by reference, discloses methods for combining previously sintered polymeric tubes in a layered fashion to achieve a unitary structure having tailored porosity characteristics. According to one embodiment of the invention, sintered polymeric tubes having differing porosity characteristics are formed using either treated resins, pastes, billets or unexpanded extrudates, singularly, or in combination with varying lubricant levels in accord with the disclosure of U.S. Pat. No. 5,433,909. The tubes so formed are then combined according to the methods of U.S. Pat. No. 5,824,050, to realize unitary prosthetic devices having the desired porosity characteristics.

More specifically, as shown at 452, the first step according to this alternative embodiment is to provide an appropriate PTFE resin. The resin is RGD treated at step 454. The RGD treated resin is then combined with a selected amount of lubricant at step 456 to form a blended paste. In an alternative embodiment, the paste is RGD treated at step 458. Regardless of whether the resin or paste is RGD treated, the blended paste is compressed into a preformed billet at step 460. If it has not been previously RGD treated at steps 454 or 458, the billet is RGD treated at step 462. Next, the preformed billet is extruded in step 464. If the components of the extrudate have not yet been RGD treated, such treatment takes place at step 566. Next, the extrudate is dried at step 568. A last chance for RGD treating occurs at step 570. In steps 572 and 574 the extrudate is expanded/stretched and sintered. The sintered tubes having different porosity and/or chemistry characteristics are combined in step 576 in accordance with the methods of U.S. Pat. No. 5,824,050 to form a prosthetic device having the desired porosity characteristics.

It will thus be seen that the invention efficiently attains the objects set forth above, including providing implantable devices having tailored porosity and/or chemistry characteristics. Since certain changes may be made in the above constructions and the described methods without departing from the scope of the invention, it is intended that all matter contained in the above description or shown in the accompanying drawings be interpreted as illustrative and not in a limiting sense. By way of example, any known methods for varying the porosity and/or chemistry characteristics of implantable prostheses, such as varying the lubrication level in the blended pasted, viewed in combination with the disclosed methods are considered to be within the scope of the present invention. Additionally, any methods for combining resins, pastes, billets or extrudates, which are treated with plasma radiation, according to the methods of the invention, are also considered to be within the scope of the present invention.

Having described the invention, what is claimed as new and protected by Letters Patent is:

1. A method comprising the steps of:
   blending a resin of a polymer with an extrusion aid to form a paste; and
   treating said paste with a plasma energy to a sufficient degree that said treatment alters at least one of a porosity characteristic and a chemistry characteristic in articles fabricated from said paste.

2. A method according to claim 1, wherein said polymer is a fluoropolymer.

3. A method according to claim 2, wherein said fluoropolymer is a homopolymer or copolymer of PTFE, FEP, and PFA.

4. A method according to claim 1, wherein said polymer is UHMWPE.

5. A method according to claim 1, wherein said step of blending said polymer resin with said extrusion aid further comprises varying an amount of said extrusion aid to select said porosity characteristic.

6. A method according to claim 1, wherein said step of plasma treating said paste further comprises at least one of plasma glow discharge treating, plasma etching, and plasma activating said paste.

7. A method according to claim 1, wherein said method further comprises:
   forming said paste into a preform billet;
   extruding said billet into an extruded shape;
   expanding said extruded shape into a porous article; and
   sintering said porous article.

8. A method according to claim 7 further comprising the step of forming a surgical implant device from said porous article.

9. A method according to claim 8, wherein said surgical implant device further comprises at least one of a vascular graft, an endovascular liner or graft, a prosthetic patch, a vascular access device, or implantable tissue augmentation device.

10. A method according to claim 7, wherein said sintered porous article is formed into a membrane.

11. A method according to claim 10, further comprising the step of employing at least one of said membrane in a diagnostic test strip.

12. A method according to claim 10, further comprising the step of employing at least one of said membrane in a filtration article.

13. A surgical implant comprising a resin of a polymer that has been shaped to form the surgical implant and that has been plasma treated to impart a porosity characteristic to said surgical implant.

14. A surgical implant according to claim 13, wherein said surgical implant comprises at least one of a vascular graft, an endovascular liner, a prosthetic patch, a vascular access device, or an implantable tissue augmentation device.

15. A surgical implant according to claim 13, further comprising a plurality of regions, wherein at least one of said regions is formed from a resin of said polymer that has not been treated with plasma.

16. A surgical implant according to claim 15, wherein each of said plurality of regions has a characteristic porosity, wherein said porosity is dependent on whether said region is formed from said resin treated with said plasma.

17. A surgical implant according to claim 15, wherein each of said plurality of regions has a characteristic permeability, wherein said characteristic permeability is dependent on whether said region is formed from said plasma treated resin.

18. A surgical implant according to claim 15, wherein each of said plurality of regions has a characteristic fibril density, wherein said characteristic fibril density is dependent on whether said region is formed from said plasma treated resin with said plasma.

19. A surgical implant according to claim 15, wherein each of said plurality of regions has a characteristic chemistry, wherein said characteristic chemistry is dependent on whether said region is formed from said resin treated with said plasma.

20. A method for producing an improved blended paste from a polymer, said method comprising:
   blending a resin of the polymer with an extrusion aid to form said blended paste, and
   treating said blended paste with plasma treatment.

21. A method for producing an improved blended paste according to claim 20, wherein said step of blending further comprises blending a fluoropolymer resin with said extrusion aid.

22. A method according to claim 21, wherein said fluoropolymer resin is a homopolymer or copolymer of PTFE, FEP, or PFA.

23. A method for producing an improved blended paste according to claim 21, wherein said blending step further comprises blending UHMWPE resin with said extrusion aid.

24. A method for producing an improved extrudate comprising:
   blending a polymer resin with an extrusion aid to form a blended paste;
   compressing said paste into a preform billet;
   extruding said billet into a shape to form an extrudate; and
   plasma treating said extrudate.

25. A method for producing a polymeric substrate having regions of differing fibril density comprising:
   plasma treating a first polymer resin;
   blending said first resin with an extrusion aid to form a treated paste;
   blending a second untreated resin of a polymer with an extrusion aid to form an untreated paste;
   disposing said treated paste along first regions of a preform mold, and said untreated paste along second regions of said preform mold;

compressing said treated and untreated pastes in said preform mold into a billet;

extruding said preform billet to form art extrudate; and expanding said extrudate to form an article having a first fibril density in regions formed from said treated paste, and a second fibril density in regions formed from said untreated paste.

26. A method for producing a porous expanded article according to claim 25, wherein said first and second polymers are a same polymer.

27. A vascular graft comprising a polymer component having been treated with plasma prior to expansion, wherein said plasma treatment effects at least one of a porosity characteristic, permeability characteristic, and a chemistry characteristic of said graft.

28. A diagnostic test strip comprising a polymer component having been treated with plasma prior to fabrication, wherein said plasma treatment effects at least one of a porosity characteristic, a permeability characteristic and a chemistry characteristic of said test strip.

29. An article of filtration comprising a polymer component having been treated with plasma prior to fabrication, wherein said plasma treatment effects at least one of a porosity characteristic, a permeability characteristic and a chemistry characteristic of said filtration article.

30. An implantable tissue augmentation device, comprising:

an inner region; and an outer region, coaxially located about said inner region and having a lower porosity than said inner region;

wherein at least one of the group of said inner region and said outer region has been subjected to plasma treatment.

31. The implantable tissue augmentation device of claim 30, wherein said implantable tissue augmentation device has a round cross-section.

32. The implantable tissue augmentation device of claim 31, wherein said inner region extends to an outer surface along a portion of a circumference of said implantable tissue augmentation device.

33. The implantable tissue augmentation device of claim 30, wherein said inner region extends to an outer surface along a portion of said implantable tissue augmentation device along a length of said implantable tissue augmentation device.

34. The implantable tissue augmentation device of claim 30, wherein said inner region is subject to plasma treatment.

35. The implantable tissue augmentation device of claim 30, wherein said outer region is subject to plasma treatment.

36. The implantable tissue augmentation device of claim 30, wherein said inner region has a continuous cross section.

37. The implantable tissue augmentation device of claim 30, wherein said inner region has an average internodal distance of approximately 150 microns.

38. The implantable tissue augmentation device of claim 30, wherein said outer region has an average internodal distance of approximately 20 microns.

39. The implantable tissue augmentation device of claim 38, wherein said inner region has an average internodal distance of approximately 150 microns.

40. The implantable tissue augmentation device of claim 38, wherein said inner region has an average internodal distance of approximately 50 to 100 microns.

41. The implantable tissue augmentation device of claim 30, wherein said outer region has an average internodal distance of approximately 20 to 30 microns.

42. The implantable tissue augmentation device of claim 41, wherein said inner region has an average internodal distance of approximately 50 to 100 microns.

43. The implantable tissue augmentation device of claim 30, wherein said outer region has an average internodal distance of approximately 5 to 10 microns.

44. The implantable tissue augmentation device of claim 43, wherein said inner region has an average internodal distance of approximately 50 to 100 microns.

45. The implantable tissue augmentation device of claim 30, wherein said inner region has an average internodal distance of approximately 50 to 500 microns.

46. The implantable tissue augmentation device of claim 30, wherein said outer region has an average internodal distance of less than 50 microns.

47. The implantable tissue augmentation device of claim 46, wherein said inner region has an average internodal distance of approximately 50 to 500 microns.

48. A surgical implant in the form of an elongated structure, comprising:

an inner region of said elongated structure;

an outer region of said elongated structure, coaxially located about said inner region and having a lower porosity than said inner region; and an outer longitudinally extending surface region having a similar composition to said inner region.

49. The surgical implant of claim 48, wherein said surgical implant has a round cross-section.

50. The surgical implant of claim 48, wherein at least one of the group of said inner region and said outer region is subject to plasma treatment.

51. The surgical implant of claim 48, wherein said inner region and said outer longitudinally extending surface region are subject to plasma treatment.

52. The surgical implant of claim 48, wherein said inner region and said outer longitudinally extending surface region have an average internodal distance of approximately 150 microns.

53. The surgical implant of claim 48, wherein said outer region has an average internodal distance of approximately 20 microns.

54. The surgical implant of claim 53, wherein said inner region and said outer longitudinally extending surface region have an average internodal distance of approximately 150 microns.

55. The implantable tissue augmentation device of claim 48, wherein said inner region has an average internodal distance of approximately 50 to 100 microns.

56. The implantable tissue augmentation device of claim 48, wherein said outer region has an average internodal distance of approximately 20 to 30 microns.

57. The implantable tissue augmentation device of claim 56, wherein said inner region has average internodal distance of approximately 50 to 100 microns.

58. The implantable tissue augmentation device of claim 48, wherein said outer region has an average internodal distance of approximately 5 to 10 microns.

* * * * *